United States Patent
Ayesa et al.

(10) Patent No.: US 8,815,809 B2
(45) Date of Patent: Aug. 26, 2014

(54) CYSTEINE PROTEASE INHIBITORS

(75) Inventors: Susana Ayesa, Huddinge (SE); Karolina Ersmark, Huddinge (SE); Urszula Grabowska, Huddinge (SE); Ellen Hewitt, Huddinge (SE); Daniel Jönsson, Huddinge (SE); Pia Kahnberg, Huddinge (SE); Björn Klasson, Huddinge (SE); Peter Lind, Huddinge (SE); Stina Lundgren, Huddinge (SE); Lourdes Odèn, Huddinge (SE); Kevin Parkes, Huddinge (SE); Daniel Wiktelius, Huddinge (SE)

(73) Assignee: Medivir UK Ltd, Little Chesterford, Essex (GB)

( * ) Notice: Subject to any disclaimer, the term of this patent is extended or adjusted under 35 U.S.C. 154(b) by 0 days.

(21) Appl. No.: 13/514,758

(22) PCT Filed: Dec. 10, 2010

(86) PCT No.: PCT/IB2010/055732
§ 371 (c)(1),
(2), (4) Date: Jul. 26, 2012

(87) PCT Pub. No.: WO2011/070539
PCT Pub. Date: Jun. 16, 2011

(65) Prior Publication Data
US 2012/0309673 A1  Dec. 6, 2012

(30) Foreign Application Priority Data

Dec. 10, 2009  (SE) .................................... 0950951-4
Jun. 16, 2010  (GB) .................................... 1010084.0

(51) Int. Cl.
| | | |
|---|---|---|
| A61K 38/00 | (2006.01) | |
| A61K 38/05 | (2006.01) | |
| C07K 5/065 | (2006.01) | |
| C07K 5/078 | (2006.01) | |
| C07K 5/062 | (2006.01) | |

(52) U.S. Cl.
CPC .............. A61K 38/05 (2013.01); C07K 5/06078 (2013.01); C07K 5/06139 (2013.01); C07K 5/06034 (2013.01); C07K 5/0606 (2013.01)
USPC ....... 514/18.3; 514/1.7; 514/21.91; 514/18.6; 514/16.6; 514/17.9; 514/1.9; 514/17.7

(58) Field of Classification Search
CPC  C07C 2101/04; C07C 237/22; C07C 271/24; C07K 5/06034; C07K 5/0606; C07K 5/06078; C07K 5/06139
See application file for complete search history.

(56) References Cited

U.S. PATENT DOCUMENTS

2011/0312964 A1* 12/2011 Ayesa et al. ................ 514/236.5
2012/0283305 A1* 11/2012 Ayesa et al. .................... 514/404

FOREIGN PATENT DOCUMENTS

| EP | 1 498 411 A1 | 1/2005 |
|---|---|---|
| WO | WO-03/024924 A1 | 3/2003 |
| WO | WO-2006102243 A2 | 9/2006 |
| WO | WO-2006102423 A1 | 9/2006 |
| WO | WO-2010070615 A1 | 6/2010 |

OTHER PUBLICATIONS

GEO Profiles, Ncbi.Nlm.Nih.Gov, available at http://www.ncbi.nlm.nih.gov/geoprofiles, keyword "Cathepsin S" (last visited Sep. 26, 2013).*
Depression and Chronic Pain, National Institutes of Mental Health (attached as pdf), available at http://www.nimh.nih.gov/health/publications/depression-and-chronic-pain/depression-and-chronic-p.pdf (last visited Sep. 26, 2013).*
Centers for Disease Control and Prevention, Cdc.Gov, available at www.cdc.gov (last visited Sep. 26, 2013).*

* cited by examiner

Primary Examiner — Christina Bradley
Assistant Examiner — Randall L Beane

(57) ABSTRACT

Compounds of Formula II

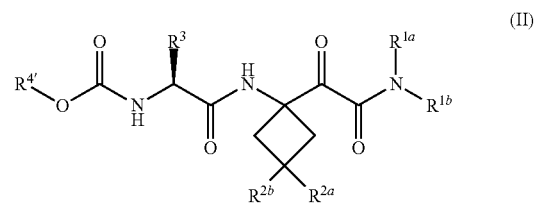

wherein
$R^{1a}$ is H; and $R^{1b}$ is $C_1$-$C_6$alkyl, Carbocyclyl or Het; or
$R^{1a}$ and $R^{1b}$ together define a saturated cyclic amine with 3-6 ring atoms;
$R^{2a}$ and $R^{2b}$ are independently H, halo, $C_1$-$C_4$alkyl, $C_1$-$C_4$haloalkyl or $C_1$-$C_4$alkoxy, or $R^{2a}$ and $R^{2b}$ together with the carbon atom to which they are attached form a $C_3$-$C_6$cycloalkyl;
$R^3$ is a branched $C_5$-$C_{10}$ alkyl chain, $C_2$-$C_4$haloalkyl or —$CH_2C_3$-$C_7$ cycloalkyl;
$R^{4'}$ is $C_1$-$C_6$alkyl, $C_1$-$C_6$haloalkyl or oxetany-3-yl.
for use in the prophylaxis or treatment of a disorder characterized by inappropriate expression or activation of cathepsin S.

17 Claims, No Drawings

CYSTEINE PROTEASE INHIBITORS

This application is the National Stage Under 35 U.S.C. §371 of PCT International Application No, PCT/IB2010/055732 filed on Dec. 10, 2010, which claims priority under 35 USC §119 of Application No. 0950951-4 filed in Sweden on Dec. 10, 2009 and of Application No. 1010084.0 filed in Great Britain on Jun. 16, 2010. The entire contents of each of which are incorporated by reference.

TECHNICAL FIELD

This invention relates to inhibitors of cathepsin S, and their use in methods of treatment for disorders involving cathepsin S such as autoimmune disorders, allergy and chronic pain conditions.

BACKGROUND TO THE INVENTION

The papain superfamily of cysteine proteases are widely distributed in diverse species including mammals, invertebrates, protozoa, plants and bacteria. A number of mammalian cathepsin enzymes, including cathepsins B, F, H, K, L, O, S, and W, have been ascribed to this superfamily, and inappropriate regulation of their activity has been implicated in a number of metabolic disorders including arthritis, muscular dystrophy, inflammation, glomerulonephritis and tumour invasion. Pathogenic cathepsin like enzymes include the bacterial gingipains, the malarial falcipains I, II, III et seq and cysteine proteases from *Pneumocystis carinii, Trypanosoma cruzei* and *brucei, Crithidia fusiculata, Schistosoma* spp.

In WO 97/40066, the use of inhibitors against Cathepsin S is described. The inhibition of this enzyme is suggested to prevent or treat disease caused by protease activity. Cathepsin S is a highly active cysteine protease belonging to the papain superfamily. Its primary structure is 57%, 41% and 45% homologous with human cathepsin L and H and the plant cysteine protease papain respectively, although only 31% homologous with cathepsin B. It is found mainly in B cells, dendritic cells and macrophages and this limited occurrence suggests the potential involvement of this enzyme in the pathogenesis of degenerative disease. Moreover, it has been found that destruction of Ii by proteolysis is required for MHC class II molecules to bind antigenic peptides, and for transport of the resulting complex to the cell surface. Furthermore, it has been found that Cathepsin S is essential in B cells for effective Ii proteolysis necessary to render class II molecules competent for binding peptides. Therefore, the inhibition of this enzyme may be useful in modulating class II-restricted immune response (WO 97/40066). Other disorders in which cathepsin S is implicated are asthma, chronic obstructive pulmonary disease, endometriosis and chronic pain.

BRIEF DESCRIPTION OF THE INVENTION

According to a first aspect of the invention there is provided a compound of Formula II:

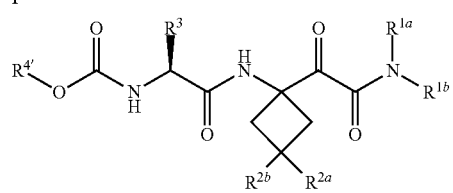

(II)

wherein
$R^{1a}$ is H; and
$R^{1b}$ is $C_1$-$C_6$alkyl, optionally substituted with 1-3 substituents independently selected from: halo, hydroxy, cyano, azido, $C_1$-$C_4$haloalkyl, $C_1$-$C_4$alkoxy, $C_1$-$C_4$haloalkoxy, $C_1$-$C_4$alkoxycarbonyl, $C_1$-$C_4$alkylcarbonyl, amine, $C_1$-$C_4$alkylamine, $C_1$-$C_4$dialkylamine, $C_1$-$C_4$alkylsulfonyl, $C_1$-$C_4$alkylsulfonylamino, aminocarbonyl, aminosulphonyl, Carbocyclyl and Het; or
$R^{1b}$ is Carbocyclyl or Het; or
$R^{1a}$ and $R^{1b}$ together with the N atom to which they are attached define a saturated cyclic amine with 3-6 ring atoms;
wherein the Carbocyclyl, Het or cyclic amine is optionally substituted with 1-3 substituents independently selected from halo, hydroxy, cyano, azido, $C_1$-$C_4$alkyl, $C_1$-$C_4$haloalkyl, $C_1$-$C_4$alkoxy, $C_1$-$C_4$haloalkoxy, $C_1$-$C_4$alkoxycarbonyl, $C_1$-$C_4$alkylcarbonyl, amine, $C_1$-$C_4$alkylamine, $C_1$-$C_4$dialkylamine, $C_1$-$C_4$alkylsulfonyl, $C_1$-$C_4$alkylsulfonylamino, aminocarbonyl, aminosulphonyl, RxOOC—$C_0$-$C_2$alkylene (where Rx is H, $C_1$-$C_4$alkyl or $C_1$-$C_4$haloalkyl), phenyl, benzyl or $C_3$-$C_6$cycloalkyl$C_0$-$C_2$alkylene;
wherein the phenyl, benzyl or cycloalkyl moiety is optionally substituted with 1-3 substituents independently selected from halo, $C_1$-$C_4$alkyl, $C_1$-$C_4$haloalkyl or $C_1$-$C_4$alkoxy);
$R^{2a}$ and $R^{2b}$ are independently selected from H, halo, $C_1$-$C_4$alkyl, $C_1$-$C_4$haloalkyl, $C_1$-$C_4$alkoxy, or $R^{2a}$ and $R^{2b}$ together with the carbon atom to which they are attached form a $C_3$-$C_6$cycloalkyl;
$R^3$ is a $C_5$-$C_{10}$ alkyl, optionally substituted with 1-3 substituents independently selected from halo, $C_1$-$C_4$haloalkyl, $C_1$-$C_4$alkoxy, $C_1$-$C_4$haloalkoxy; or
$R^3$ is a $C_2$-$C_4$alkyl chain with at least 2 chloro or 3 fluoro substituents; or
$R^3$ is $C_3$-$C_7$cycloalkylmethyl, optionally substituted with 1-3 substituents independently selected from $C_1$-$C_4$alkyl, halo, $C_1$-$C_4$haloalkyl, $C_1$-$C_4$alkoxy, $C_1$-$C_4$haloalkoxy;
$R^{4'}$ is $C_1$-$C_6$alkyl, $C_1$-$C_6$haloalkyl or oxetan-3-yl.
Het is a stable, monocyclic or bicyclic, saturated, partially saturated or aromatic ring system containing 1-4 heteroatoms independently selected from O, S and N, each ring having 5 or 6 ring atoms;
Carbocyclyl is $C_3$-$C_6$cycloalkyl, $C_5$-$C_6$cycloalkenyl or phenyl;
or a pharmaceutically acceptable salt, hydrate or N-oxide thereof.

In some embodiments, $R^{1a}$ is H and $R^{1b}$ is $C_1$-$C_4$alkyl, such as methyl, ethyl, isopropyl, t-butyl or preferably methyl, optionally substituted with one or more substituents as defined above, preferably 1-3 halo (e.g. F) or a $C_1$-$C_4$alkoxy (e.g. methoxy) group.

In other embodiments $R^{1a}$ is H and $R^{1b}$ is methyl, cyclopropyl, 1-phenylethyl, or a 5 or 6 membered heterocyclic ring containing 1-3 nitrogen atoms and 0 or 1 sulphur atoms, the cyclopropyl, phenyl or heterocyclic ring being optionally substituted with up to three substituents independently selected from:
$C_1$-$C_4$alkyl, halo, $C_1$-$C_4$haloalkyl, $C_1$-$C_4$alkoxy, $C_1$-$C_4$haloalkoxy, $C_1$-$C_4$alkoxycarbonyl, $C_1$-$C_4$alkylcarbonyl, amine, $C_1$-$C_4$alkylamine, $C_1$-$C_4$dialkylamine, $C_1$-$C_4$alkylsulfonyl, $C_1$-$C_4$alkylsulfonylamino, aminocarbonyl, aminosulphonyl, RxOOC—$C_0$-$C_2$alkylene (where Rx is H or $C_1$-$C_4$alkyl) or $C_3$-$C_6$cycloalkyl$C_0$-$C_2$alkylene or benzyl (the cycloalkyl, or the phenyl ring of the benzyl being optionally substituted with 1-3 substituents selected from $C_1$-$C_4$alkyl, halo, $C_1$-$C_4$haloalkyl, $C_1$-$C_4$alkoxy, $C_1$-$C_4$haloalkoxy).

Examples of the 5 or 6 membered aromatic heterocyclyl for $R^{1b}$ include pyridyl or pyrimidyl and especially pyrrolyl, pyrazolyl, imidazolyl, thiazolyl, thiadiazolyl, triazolyl or tetrazolyl, optionally substituted with any of which is optionally substituted with $C_1$-$C_4$alkyl (e.g. Me), halo (e.g. F), $C_1$-$C_4$haloalkyl (e.g. $CF_3$), $C_1$-$C_4$alkoxy (e.g. MeO), $C_3$-$C_6$cycloalkyl$C_0$-$C_1$alkylene (e.g. cyclopropyl or cyclopropylmethyl, benzyl or $C_0$-$C_2$alkyleneCOOH and its $C_1$-$C_4$alkyl esters. An exemplary species is 1-methyl-pyrazol-5-yl.

Typically according to this embodiment, the heterocyclic ring is pyrrolyl, pyrazolyl, imidazolyl, triazolyl, thiazolyl or thiadiazolyl, any of which is optionally substituted with $C_1$-$C_4$alkyl, halo, $C_1$-$C_4$haloalkyl, $C_1$-$C_4$alkoxy, $C_3$-$C_6$cycloalkyl or $C_3$-$C_6$cycloalkylmethyl.

Typically according to this embodiment, the heterocyclic ring is pyrazol-1-yl, which is optionally substituted with $C_1$-$C_4$alkyl, halo, $C_1$-$C_4$haloalkyl or cyclopropyl, preferably $C_1$-$C_4$alkyl, such as ethyl or preferably methyl.

A preferred value for $R^{1b}$ is pyrazol-1-yl which is N-substituted with $C_1$-$C_4$alkyl, such as ethyl or methyl.

A further typical value for $R^{1b}$ according to this embodiment, is methyl or cyclopropyl.

In other embodiments $R^{1a}$ is H and $R^{1b}$ is methyl or ethyl which is substituted in the 1-position with a cyclic group such as phenyl, or $R^{1b}$ is a monocyclic heterocyclyl such as pyrrolidinyl, piperidinyl, morpholinyl, thiomorpholinyl, piperazinyl, indolinyl, pyranyl, tetrahydropyranyl, tetrahydrothiopyranyl, thiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyridazinyl, tetrazolyl, pyrazolyl, indolyl and the like. The phenyl or heterocyclyl is optionally substituted, for example with 1-3 substituents independently selected from hydroxy, amino, $C_1$-$C_4$alkyl, halo, $C_1$-$C_4$haloalkyl, $C_1$-$C_4$alkoxy, amino, $C_1$-$C_4$alkylamine, $C_1$-$C_4$dialkylamine and the like. An exemplary species is 1-phenylethyl.

In other embodiments $R^{1a}$ is H and $R^{1b}$ is $C_3$-$C_6$cycloalkyl, preferably cyclobutyl or cyclopropyl, optionally substituted as defined above. Preferably the cycloalkyl is unsubstituted or substituted with 1-3 substituents selected from halo (e.g. 1 or 2 fluoro), hydroxy, $C_1$-$C_4$alkyl (e.g. 1 or 2 methyl), $C_1$-$C_4$haloalkyl (e.g. a $CF_3$ group) $C_1$-$C_4$alkoxy (e.g. an MeO group), $C_1$-$C_4$alkylamine (e.g. an MeNH— group), $C_1$-$C_4$dialkylamine (e.g. an $(Me)_2N$— group) and the like. An exemplary species is cyclopropyl, or monofluoro- or gemdifluorocyclopropyl.

In some embodiments, $R^{1a}$ is H and $R^{1b}$ is a 6 or preferably 5 membered aromatic, heterocyclic ring containing 1-3 nitrogen atoms and 0 or 1 sulphur atoms, optionally substituted as defined above. Preferably the heterocyclic ring is linked to the adjacent nitrogen atom of the alpha keto amide group through a carbon atom of the heterocyclic ring. Exemplary substituents include $C_1$-$C_4$alkyl, halo, $C_1$-$C_4$haloalkyl, $C_1$-$C_4$alkoxy, $C_1$-$C_4$haloalkoxy, $C_1$-$C_4$alkoxycarbonyl, $C_1$-$C_4$alkylcarbonyl, amine, $C_1$-$C_4$alkylamine, di$C_1$-$C_4$alkylamine, $C_1$-$C_4$alkylsulfonyl, $C_1$-$C_4$alkylsulfonylamino, aminocarbonyl, aminosulphonyl, RxOC(=O)$C_0$-$C_2$alkylene (where Rx is H or $C_1$-$C_4$alkyl) or $C_3$-$C_6$cycloalkyl$C_0$-$C_2$alkylene or benzyl (the cycloalkyl or the phenyl ring of benzyl group) being optionally substituted with 1-3 substituents selected from $C_1$-$C_4$alkyl, halo, $C_1$-$C_4$haloalkyl, $C_1$-$C_4$alkoxy, $C_1$-$C_4$haloalkoxy)

In some embodiments, $R^{1a}$, $R^{1b}$ and the N-atom to which they are attached form a 3-6 membered cyclic amine, such as aziridine, azetidine, pyrrolidine, and preferably morpholine, piperazine or piperidine. These cyclic amines may be unsubstituted or substituted as described above, preferably with 1-3 substituents selected from halo (e.g. 1 or 2 fluoro), hydroxy, $C_1$-$C_4$alkyl (e.g. 1 or 2 methyl), $C_1$-$C_4$haloalkyl (e.g. a $CF_3$ group) $C_1$-$C_4$alkoxy (e.g. an MeO-group), $C_1$-$C_4$alkylamine (e.g. an MeNH— group), $C_1$-$C_4$dialkylamine (e.g. an $(Me)_2N$— group) and the like.

In some embodiments $R^3$ is cycloalkylalkyl, optionally substituted, for example with halo, (such as F) or alkoxy (such as MeO). Exemplary species include 1-methylcyclopentylmethyl, 1-methylcyclohexylmethyl, 1-methylcyclobutylmethyl, 1-methyl-3,3-difluorocyclobutylmethyl, 1-methyl-4,4-difluorocyclohexylmethyl, cyclopropylmethyl or 1-methyl-3,3-difluorocyclopentylmethyl.

Preferred $R^3$ species include t-butylmethyl, cyclobutylmethyl, 1-methylcyclobutylmethyl and 1-methylcyclopentylmethyl, any of which is optionally substituted with one or two F or MeO. Representative species are 1-fluorocyclobutylmethyl and 1-fluorocyclopentylmethyl.

Further representative $R^3$ species include 1-methylcyclopentylmethyl and 1-fluorocyclopentylmethyl, Other embodiments have $R^3$ as a straight or branched alkyl chain of 5-10 C-atoms, optionally substituted with 1-3 halo, (e.g. Cl or F), or a $C_1$-$C_4$alkoxy (e.g. MeO). Exemplary species include 2,2-dimethylpropyl, 3,3-dimethylpentyl, 2,2,3,3-tetramethylbutyl. Exemplary species of halogenated alkyl include 2,2-dichloroethyl, 3,3,3-trifluoropropyl, 2,2-trifluoromethylethyl, or 2,2,2-trifluoroethyl.

Typically $R^{4'}$ is $C_1$-$C_4$alkyl, such as methyl or ethyl.

Alternatively according $R^{4'}$ is $C_1$-$C_6$haloalkyl, such as $C_1$-$C_6$-chloroalkyl or $C_1$-$C_6$-fluoroalkyl.

One embodiment of the invention includes compounds of Formula II, wherein at least one of $R^{2a}$ and $R^{2b}$ is halo, $C_1$-$C_4$alkyl, $C_1$-$C_4$haloalkyl or $C_1$-$C_4$alkoxy. Typically according to this embodiment, one of $R^{2a}$ and $R^{2b}$ is H, and the other is chloro, fluoro, trifluoromethyl or methoxy; especially fluoro or methoxy.

A preferred embodiment of the invention includes compounds of Formula II wherein one of $R^{2a}$ and $R^{2b}$ is H, and the other is F. Specially preferred according to this embodiment are compounds having the stereochemistry shown in Formula IIa:

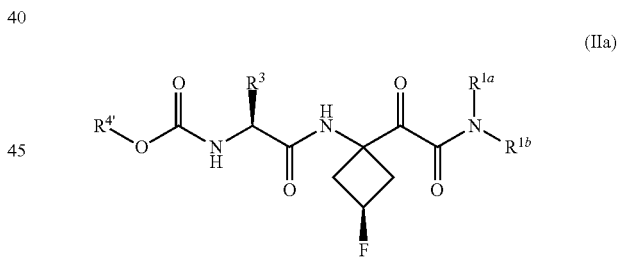

(IIa)

Another embodiment of the invention includes compounds of Formula II, wherein $R^{2a}$ and $R^{2b}$ are both F, thus providing compounds of Formula IIb:

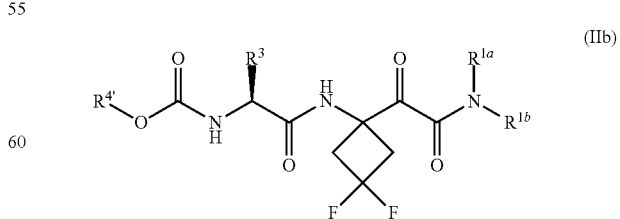

(IIb)

A further embodiment of the invention includes compounds wherein $R^{2a}$ and $R^{2b}$ are both H, thus providing compounds of Formula IIc:

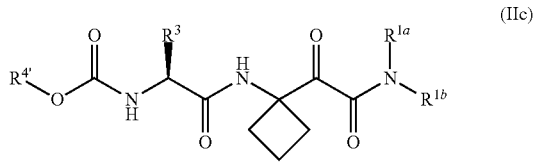

In other embodiments $R^{2a}$ and $R^{2b}$ together with the carbon atom to which they are attached form a $C_3$-$C_6$cycloalkyl.

A further embodiment of the invention includes compounds of Formula II wherein $R^{1a}$ is H, $R^{1b}$ is N-methylpyrazol-2-yl, $R^{2a}$ and $R^{2b}$ are both H and $R^3$ is cyclopentylmethyl which is substituted with methyl or fluoro, thus affording compounds of Formula IId:

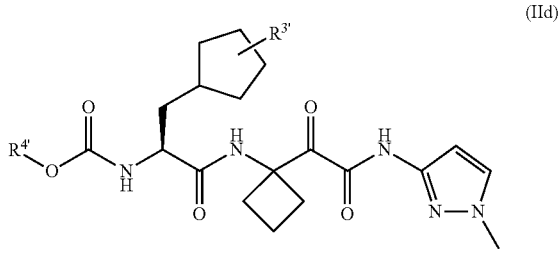

wherein $R^{3'}$ is methyl or fluoro.

One embodiment of the invention includes compounds of Formula IId, with the proviso that $R^{4'}$ is not methoxy or ethoxy.

An alternative embodiment of the invention includes compounds of Formula IId wherein $R^{4'}$ is methoxy or ethoxy, thus affording compounds of Formula III:

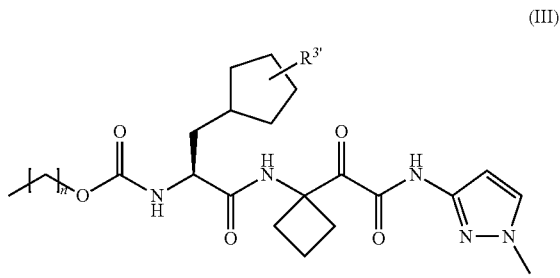

wherein n is 0 or 1.

One embodiment of the invention includes compounds of Formula III with the proviso that the compound is not ethyl 3-(1-fluorocyclopentyl)-1-(1-(2-(1-methyl-1H-pyrazol-3-ylamino)-2-oxoacetyl)cyclobutylamino)-1-oxopropan-2-ylcarbamate.

An alternative embodiment of the invention includes the compound ethyl 3-(1-fluorocyclopentyl)-1-(1-(2-(1-methyl-1H-pyrazol-3-ylamino)-2-oxoacetyl)cyclobutylamino)-1-oxopropan-2-ylcarbamate, i.e. the compound of Formula IV:

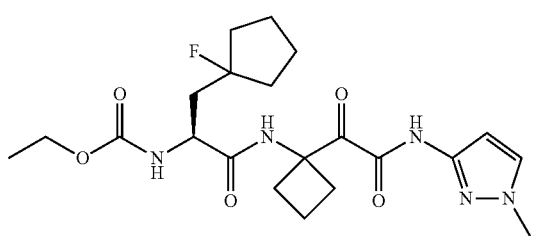

The compounds of Formula II are characterised by various advantageous pharmaceutical properties and exhibit at least one improved property in view of the compounds of the prior art. In particular, the inhibitors of the present invention are superior in one or more of the following pharmacological related properties, i.e. potency, decreased cytotoxicity, improved pharmacokinetics, acceptable dosage and pill burden.

Without in any way wishing to be bound by theory, or the ascription of tentative binding modes for specific variables, P1, P2 and P3 as used herein are provided for convenience only and have their conventional meanings and denote those portions of the inhibitor believed to fill the S1, S2 and S3 subsites respectively of the enzyme, where S1 is adjacent the cleavage site and S3 remote from the cleavage site.

A further aspect of the invention comprises a method employing the compounds of Formula II for the prophylaxis or treatment of diseases caused by aberrant expression or activation of cathepsin, i.e. diseases or conditions alleviated or modified by inhibition of cathepsin S, preferably without substantial concomitant inhibition of other members of the papain superfamily.

A further aspect of the invention provides the use of the compounds of Formula II prophylaxis or treatment of diseases caused by aberrant expression or activation of cathepsin, ie diseases or conditions alleviated or modified by inhibition of cathepsin S, preferably without substantial concomitant inhibition of other members of the papain superfamily.

A further aspect of the invention provides the use of the compounds of Formula II for the manufacture of a medicament for the prophylaxis or treatment of diseases caused by aberrant expression or activation of cathepsin S, i.e. diseases or conditions alleviated or modified by inhibition of cathepsin S, preferably without substantial concomitant inhibition of other members of the papain superfamily.

Examples of such diseases or conditions defined in the immediately preceding three paragraphs include those enumerated in WO 97/40066, such as autoimmune diseases, allergies, such as asthma and hay fever, multiple sclerosis, rheumatoid arthritis and the like. A further example is the treatment of endometriosis, and especially chronic pain, as disclosed in WO03/20287. The invention further provides the use of the compounds of Formula II or any subgroup of Formula II in therapy and in the manufacture of a medicament for the treatment of diseases or conditions alleviated or moderated by inhibition of cathepsin S.

In one series of embodiments, the methods are employed to treat mammals, particularly humans at risk of, or afflicted with, autoimmune disease. By autoimmunity is meant the phenomenon in which the host's immune response is turned against its own constituent parts, resulting in pathology. Many human autoimmune diseases are associated with certain class II MHC-complexes. This association occurs because the structures recognized by T cells, the cells that cause autoimmunity, are complexes comprised of class II MHC molecules and antigenic peptides. Autoimmune disease can result when T cells react with the host's class II MHC molecules when complexed with peptides derived from the host's own gene products. If these class II MHC/antigenic peptide complexes are inhibited from being formed, the autoimmune response is reduced or suppressed. Any autoimmune disease in which class II MHC/antigenic complexes play a role may be treated according to the methods of the present invention.

Such autoimmune diseases include, e.g., juvenile onset diabetes (insulin dependent), multiple sclerosis, pemphigus vulgaris, Graves' disease, myasthenia gravis, systemic lupus erythematosus, rheumatoid arthritis and Hashimoto's thyroiditis.

In another series of embodiments, the methods are employed to treat mammals, particularly humans, at risk of, or afflicted with, allergic responses. By "allergic response" is meant the phenomenon in which the host's immune response to a particular antigen is unnecessary or disproportionate, resulting in pathology. Allergies are well known in the art, and the term "allergic response" is used herein in accordance with standard usage in the medical field.

Examples of allergies include, but are not limited to, allergies to pollen, "ragweed," shellfish, domestic animals (e.g., cats and dogs), bee venom, house dust mite allergens and the like. Another particularly contemplated allergic response is that which causes asthma. Allergic responses may occur, in man, because T cells recognize particular class II MHC/antigenic peptide complexes. If these class II MHC/antigenic peptide complexes are inhibited from being formed, the allergic response is reduced or suppressed. Any allergic response in which class II MHC/antigenic peptide complexes play a role may be treated according to the methods of the present invention. Immunosuppression by the methods of the present invention will typically be a prophylactic or therapeutic treatment for severe or life-threatening allergic responses, as may arise during asthmatic attacks or anaphylactic shock.

In another series of embodiments, the methods are employed to treat mammals, particularly humans, which have undergone, or are about to undergo, an organ transplant or tissue graft. In tissue transplantation (e.g., kidney, lung, liver, heart) or skin grafting, when there is a mismatch between the class II MHC genotypes (HLA types) of the donor and recipient, there may be a severe "allogeneic" immune response against the donor tissues which results from the presence of non-self or allogeneic class II MHC molecules presenting antigenic peptides on the surface of donor cells. To the extent that this response is dependent upon the formation of class II MHC/antigenic peptide complexes, inhibition of cathepsin S may suppress this response and mitigate the tissue rejection. An inhibitor of cathepsin S can be used alone or in conjunction with other therapeutic agents, e.g., as an adjunct to cyclosporin A and/or antilymphocyte gamma globulin, to achieve immunosuppression and promote graft survival. Preferably, administration is accomplished by systemic application to the host before and/or after surgery. Alternatively or in addition, perfusion of the donor organ or tissue, either prior or subsequent to transplantation or grafting, may be effective.

The above embodiments have been illustrated with an MHC class II mechanism but the invention is not limited to this mechanism of action. Suppression of cathepsin S as a treatment of COPD or chronic pain may not, for example, involve MHC class II at all.

A related aspect of the invention is directed to a method of treating a patient undergoing a therapy wherein the therapy causes an immune response, preferably a deleterious immune response, in the patient comprising administering to the patient a compound of Formula II or a pharmaceutically acceptable salt, n-oxide or hydrate thereof. Typically, the immune response is mediated by MHC class II molecules. The compound of this invention can be administered prior to, simultaneously, or after the therapy. Typically, the therapy involves treatment with a biologic, such as a protein, preferably an antibody, more preferably a monoclonal antibody. More preferably, the biologic is Remicade®, Refacto®, ReferonA®, Factor VIII, Factor VII, Betaseron®, Epogen®, Enbrel®, Interferon beta, Botox®, Fabrazyme®, Elspar®, Cerezyme®, Myobloc®, Aldurazyme®, Verluma®, Interferon alpha, Humira®, Aranesp®, Zevalin® or OKT3. Alternatively the treatment involves use of heparin, low molecular weight heparin, procainamide or hydralazine.

Assays for the assessment of cathepsin S inhibitors in the treatment of chronic pain, including neuropathic or inflammatory pain are as described in WO 03/20287.

Currently preferred indications treatable in accordance with the present invention include:
Psoriasis;
Autoimmune indications, including idiopathic thrombocytopenic purpura (ITP), rheumatoid arthritis (RA), multiple sclerosis (MS), myasthenia gravis (MG), Sjögrens syndrome, Grave's disease and systemic lupus erythematosis (SLE);
Non-autoimmmune indications include allergic rhinitis, asthma, arteriosclerosis, chronic obstructive pulmonary disease (COPD) and chronic pain.

The compounds of the invention can form salts which form an additional aspect of the invention. Appropriate pharmaceutically acceptable salts of the compounds of the invention include salts of organic acids, especially carboxylic acids, including but not limited to acetate, trifluoroacetate, lactate, gluconate, citrate, tartrate, maleate, malate, pantothenate, isethionate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, propionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids.

The compounds of the invention may in some cases be isolated as the hydrate. Hydrates are typically prepared by recrystallisation from an aqueous/organic solvent mixture using organic solvents such as dioxin, tetrahydrofuran or methanol. Hydrates can also be generated in situ by administration of the corresponding keton to a patient.

The N-oxides of compounds of the invention can be prepared by methods known to those of ordinary skill in the art. For example, N-oxides can be prepared by treating an unoxidized form of the compound of the invention with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds of the invention can be prepared from the N-oxide of an appropriate starting material.

Compounds of the invention in unoxidized form can be prepared from N-oxides of the corresponding compounds of the invention by treating with a reducing agent (e.g., sulphur, sulphur dioxide, triphenyl phosphine, lithium borohydride, sodium borohydride, phosphorus dichloride, tribromide, or the like) in an suitable inert organic solvent (e.g., acetonitrile, ethanol, aqueous dioxane, or the like) at 0 to 80° C.

The present invention also includes isotope-labelled compounds of Formula II or any subgroup of Formula II, wherein one or more of the atoms is replaced by an isotope of that atom, i.e. an atom having the same atomic number as, but an atomic mass different from, the one(s) typically found in nature. Examples of isotopes that may be incorporated into the compounds of Formula II or any subgroup of Formula II, include but are not limited to isotopes of hydrogen, such as $^2$H and $^3$H (also denoted D for deuterium and T for tritium respectively), carbon, such as $^{11}$C, $^{13}$C and $^{14}$C, nitrogen, such as $^{13}$N and $^{15}$N, oxygen, such as $^{15}$O, $^{17}$O and $^{18}$O, phosphorus, such as $^{31}$P and $^{32}$P, sulphur, such as $^{35}$S, fluorine, such as $^{18}$F, chlorine, such as $^{36}$Cl, bromine such as $^{75}$Br, $^{76}$Br, $^{77}$Br and $^{82}$Br, and iodine, such as $^{123}$I, $^{124}$I, $^{125}$I and $^{131}$I.

The choice of isotope included in an isotope-labelled compound will depend on the specific application of that compound. For example, for drug or substrate tissue distribution assays, compounds wherein a radioactive isotope such as $^3$H or $^{14}$C is incorporated will generally be most useful. For radio-imaging applications, for example positron emission tomography (PET) a positron emitting isotope such as $^{11}$C, $^{18}$F, $^{13}$N or $^{15}$O will be useful. The incorporation of a heavier isotope, such as deuterium, i.e. $^2$H, may provide greater metabolic stability to a compound of Formula II or any subgroup of Formula II, which may result in, for example, an increased in vivo half life of the compound or reduced dosage requirements. For example, $^2$H isotope(s) are typically incorporated at position(s) disposed to metabolic liability. In the compounds of the present invention, suitable positions for incorporation of $^2$H isotopes are e.g. as substituents to the cyclobutylene group, i.e. one or both of $R^{2a}$ and $R^{2b}$ is $^2$H.

Isotopically labelled compounds of Formula II or any subgroup of Formula II can be prepared by processes analogous to those described in the Schemes and/or Examples herein below by using the appropriate isotopically labelled reagent or starting material instead of the corresponding non-isotopically labelled reagent or starting material, or by conventional techniques known to those skilled in the art.

It should be noted that the radical positions on any molecular moiety used in the definitions may be anywhere on such moiety as long as it is chemically stable.

As used herein, the following terms have the meanings as defined below:

$C_m$-$C_n$alkyl used on its own or in composite expressions such as $C_m$-$C_n$haloalkyl, $C_m$—$C_n$alkylcarbonyl, $C_m$-$C_n$alkylamine, $C_m$-$C_n$alkylsulphonyl, $C_m$-$C_n$alkylsulfonylamino etc. represents a straight or branched alkyl radical having the number of carbon atoms designated, e.g. $C_1$-$C_4$alkyl means an alkyl radical having from 1 to 4 carbon atoms. Preferred alkyl radicals for use in the present invention are $C_1$-$C_4$alkyl and includes methyl, ethyl, n-propyl, isopropyl, t-butyl, n-butyl and isobutyl. Methyl and t-butyl are typically preferred. $C_1$-$C_6$alkyl has a corresponding meaning, including also all straight and branched chain isomers of pentyl and hexyl. Other recitals of $C_m$-$C_n$alkyl, such as $C_5$-$C_{10}$ alkyl have the corresponding meaning.

The term Me means methyl, MeO means methoxy, Et means ethyl and Ac means acetyl.

$C_0$-$C_2$alkylene used in composite expressions such as $C_3$-$C_6$cycloalkyl$C_0$-$C_2$alkylene refers to a divalent radical derived from a methyl or ethyl group, or in the case of $C_0$ the term $C_0$-$C_2$alkylene means a bond.

$C_1$-$C_4$haloalkyl refers to a $C_1$-$C_4$alkyl radical, wherein at least one C atom is substituted with a halogen, preferably chloro or fluoro. Trifluoromethyl is typically preferred $C_1$-$C_4$alkoxy represents a radical $C_1$-$C_4$alkyl-O wherein $C_1$-$C_4$alkyl is as defined above, and includes methoxy, ethoxy, n-propoxy, isopropoxy, t-butoxy, n-butoxy and isobutoxy. Methoxy and isopropoxy are typically preferred. $C_1$-$C_6$alkoxy has a corresponding meaning, expanded to include all straight and branched chain isomers of pentoxy and hexoxy. Other recitals of $C_m$-$C_n$alkoxy, such as $C_5$-$C_{10}$alkoxy have the corresponding meaning.

$C_1$-$C_4$haloalkoxy as used herein is meant to include $C_1$-$C_4$alkoxy wherein at least one C-atom is substituted with one or more halogen atom(s), typically chloro or fluoro. In many cases trifluoromethyl is preferred.

$C_1$-$C_4$alkoxycarbonyl means a radical $C_1$-$C_4$alkyl-O—C (=O).

Carbocyclyl includes cyclopentyl, cyclohexyl and especially cyclopropyl and cyclobutyl. Carbocyclyl further includes cyclopentenyl and cyclohexenyl, in each case with a single double bond. A frequently preferred value for Carbocyclyl is phenyl.

Cyclic amine includes aziridine, azetidine, pyrrolidine, piperidine, piperazine and morpholine.

Het is a stable, monocyclic or bicyclic, saturated, partially saturated or aromatic ring system, containing 1-4 hetero atoms independently selected from O, S and N, and each ring having 5 or 6 ring atoms; Exemplary aromatic Het include furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole and the like. Exemplary unsaturated Het include tetrahydrofuran, pyran, dihydropyran, 1,4-dioxane, 1,3-dioxane, piperidine, pyrrolidine, morpholine, tetrahydrothiopyran, tetrahydrothiophene, 2-H-pyrrole, pyrroline, pyrazoline, imidazoline, thiazolidine, isoxazolidine and the like.

The compounds of the invention include a number of handles such as OH, NH or COOH groups to which conventional prodrug moieties can be applied. Prodrugs are typically hydrolysed in vivo to release the parent compound in the plasma, liver or intestinal wall. Favoured prodrugs are esters of hydroxyl groups such as a phenolic hydroxyl group at $R^4$, or amine functions such as a sulphonamide amine function. Preferred pharmaceutically acceptable esters include those derived from $C_1$-$C_6$ carboxylic acids such as acetyl or pivaloyl or optionally substituted benzoic acid esters, preferably unsubstituted or substituted with substituents broadly as described for $R^{1a}$, typically 1-3 halo (e.g. F), $C_1$-$C_4$alkyl (e.g. Me), $C_1$-$C_4$haloalkyl (e.g. CF$_3$) or $C_1$-$C_4$alkyloxy (e.g. MeO) groups. Favoured sulphonamide prodrugs include aminoacyls derived from $C_1$-$C_6$ carboxylic acids such as acetyl or pivaloyl or optionally substituted benzoic acid esters, preferably unsubstituted or substituted with substituents broadly as described for variable $R^{1a}$, typically 1-3 halo (e.g. F), $C_1$-$C_4$alkyl (e.g. Me), $C_1$-$C_4$haloalkyl (e.g. CF$_3$) or $C_1$-$C_4$alkyloxy (e.g. MeO) groups.

Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Compounds of the invention can be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diasteromeric derivatives of compounds of Formula II, dissociable complexes are preferred (e.g., crystalline; diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography, for example HPLC or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

While it is possible for the active agent to be administered alone, it is preferable to present it as part of a pharmaceutical formulation. Such a formulation will comprise the above defined active agent together with one or more acceptable carriers/excipients and optionally other therapeutic ingredients. The carrier(s) must be acceptable in the sense of being compatible with the other ingredients of the formulation and not deleterious to the recipient.

The formulations include those suitable for rectal, nasal, topical (including buccal and sublingual), vaginal or parenteral (including subcutaneous, intramuscular, intravenous and intradermal) administration, but preferably the formulation is an orally administered formulation. The formulations may conveniently be presented in unit dosage form, e.g. tablets and sustained release capsules, and may be prepared by any methods well known in the art of pharmacy. Such methods include the step of bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of Formula II or its pharmaceutically acceptable salt in conjunction or association with a pharmaceutically acceptable carrier or vehicle. If the manufacture of pharmaceutical formulations involves intimate mixing of pharmaceutical excipients and the active ingredient in salt form, then it is often preferred to use excipients which are non-basic in nature, i.e. either acidic or neutral.

Formulations for oral administration in the present invention may be presented as discrete units such as capsules, cachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion and as a bolus etc.

With regard to compositions for oral administration (e.g. tablets and capsules), the term suitable carrier includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring or the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatine and glycerine, or sucrose and acacia; and mouthwashes comprising the active agent in a suitable liquid carrier.

As with all pharmaceuticals, the appropriate dosage for the compounds or formulations of the invention will depend upon the indication, the severity of the disease, the size and metabolic vigour and the patient, the mode of administration and is readily determined by conventional animal trials. Dosages providing intracellular (for inhibition of physiological proteases of the papain superfamily) concentrations of the order 0.01-100 µM, more preferably 0.01-10 µM, such as 0.1-5 µM are typically desirable and achievable.

Compounds of the invention are prepared by a variety of solution and solid phase chemistries.

A typical first step is the preparation of a P1 building block of the formula V

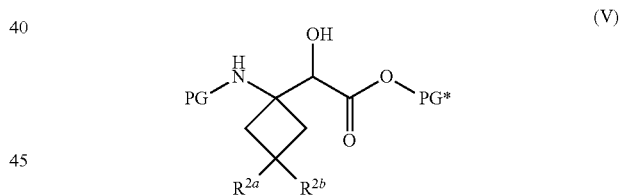

(V)

where $R^{2a}$ and $R^{2b}$ are as defined above, PG is a conventional N protecting group such as Boc, CBz or Fmoc and PG* is H or a conventional carboxy protecting group, such as a $C_1$-$C_4$alkyl or benzyl. These building blocks are novel and constitute a further aspect of the invention.

Building blocks of formula V are typically prepared as described in scheme 1 below.

Scheme 1

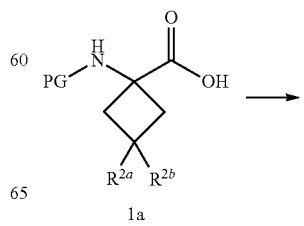

1a

-continued

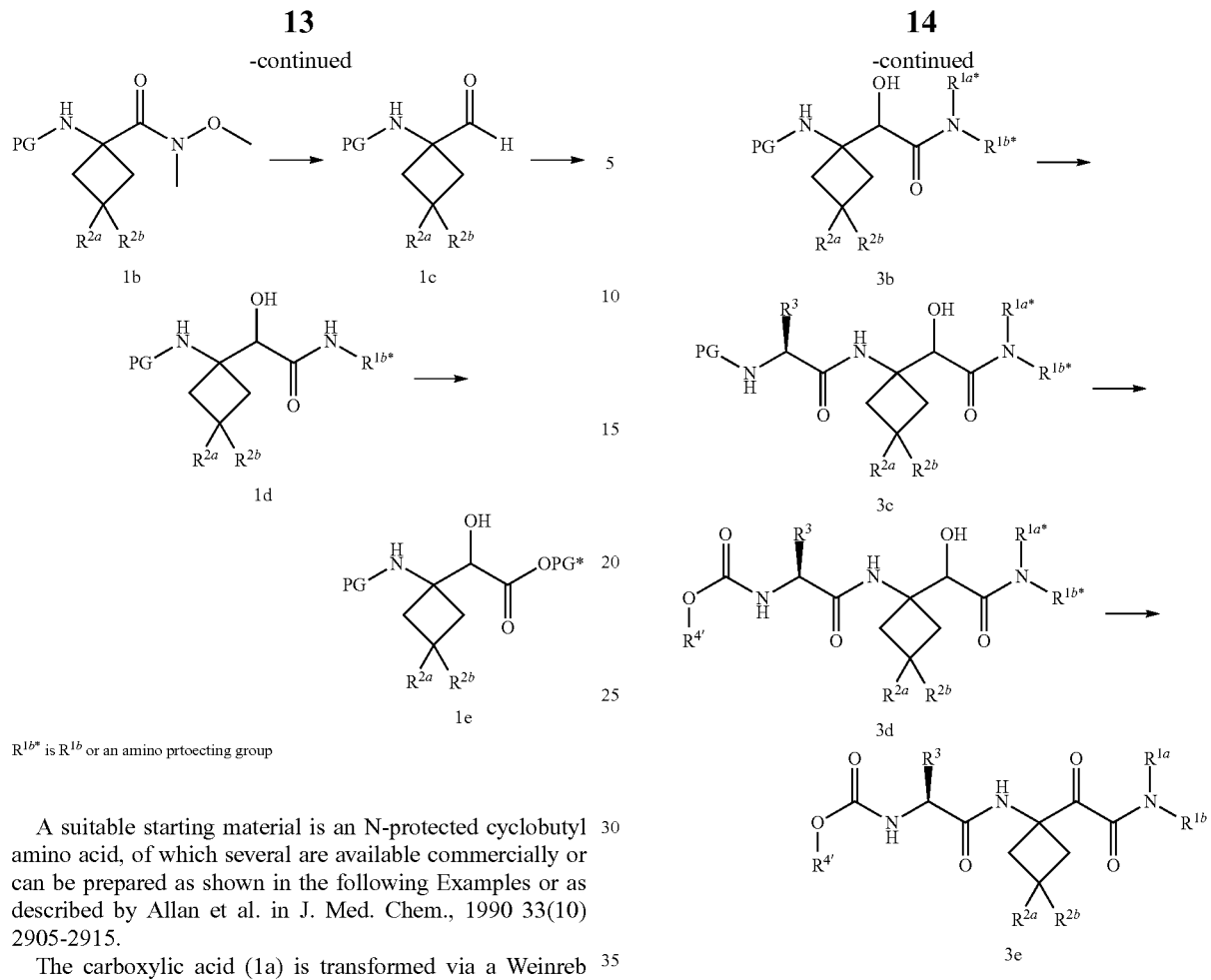

$R^{1b*}$ is $R^{1b}$ or an amino prtoecting group

A suitable starting material is an N-protected cyclobutyl amino acid, of which several are available commercially or can be prepared as shown in the following Examples or as described by Allan et al. in J. Med. Chem., 1990 33(10) 2905-2915.

The carboxylic acid (1a) is transformed via a Weinreb synthesis to a N,O-dimethylhydroxamic acid (1b) which provides the corresponding aldehyde (1c). The aldehyde may also be accessed by reduction of the carboxylic function of a cyclobutyl amino acid and oxidation under Dess Martin conditions. The aldehyde (1c) can be subsequently reacted with the appropriate isocyanide in a Passerini reaction to afford the required α-hydroxy $R^{1a}R^{1b}$ amide (1d). However, in the case where the appropriate isocyanide is not readily available, t-butylisocyanide can alternatively be used, thus affording the t-butyl amide, which after hydrolysis of the amide, provides the α-hydroxycarboxylic acid P1 building block (1e). Generally the strongly acidic conditions required to hydrolyse the amide also lead to loss of the NBoc protection, if used, hence, the amine can be used directly to couple to a P2 building block or else if it needs to be stored, the amine can be reprotected.

The P1 building block thus afforded is then extended at the C and N termini to provide compounds of Formula II as generally illustrated in scheme 3.

Scheme 3

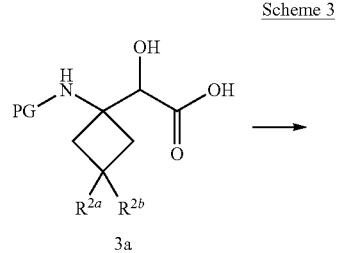

$R^{4'}$ is $C_1$—$C_6$alkyl or $C_1$—$C_6$haloalkyl

Typically the C terminus is extended first by reaction of the building block of formula V (3a) with an $R^{1a*}$ $R^{1b*}$ amine, where $R^{1a*}$ and $R^{1b*}$ are $R^{1a}$ and $R^{1b}$ respectively or synthons therefore (selected in view of the sensitivity of the $R^{1b}$ function for the P3 elongation conditions outlined below). The reaction proceeds with conventional peptide chemistries as discussed below. The thus prepared P1-prime side unit (3b) is thereafter deprotected at the N terminus and elongated with the P2 building block, providing the N-protected intermediate amine (3c). For example a P2 residue can be introduced via BocP2-OH using standard coupling conditions such as HATU, DIPEA in DMF. Removal of the N-protecting group using standard techniques well known in the art of peptide synthesis, such as treatment with acid in the case of a boc-protecting group, followed by reaction with a suitable alkoxy-carbonylating agent such as an alkyl chloroformate or a dialkyl dicarbonate, optionally in the presence of a base such as diisopropylethyl amine or similar, provides the carbamate 3d. Oxidation of the α-hydroxy group and conversion of the $R^{1a*}$ and $R^{1b*}$ synthons if present, as described above, provides the final α-keto amide derivative 3e.

An extensive range of appropriately protected L-amino acids suitable for P2 building blocks and carboxylic acids, carboxylic acid halides and carbamoyl halides suitable for P3 building blocks are commercially available or accessed by simple chemistries or as shown in WO06/064286. The P3 and P2 building blocks may alternatively be coupled first and then reacted with the P1-prime side unit.

Elongation is typically carried out in the presence of a suitable coupling agent e.g., benzotriazole-1-yloxytrispyrrolidinophosphonium hexafluorophosphate (PyBOP), O-benzotriazol-1-yl-N,N,N',N'-tetramethyl-uronium hexafluorophosphate (HBTU), O-(7-azabenzotriazol-1-yl)-1,1,3,3-tetramethyl-uronium hexafluorophosphate (HATU), 1-(3-dimethylaminopropyl)-3-ethylcarbodiimide hydrochloride (EDC), or 1,3-dicyclohexyl carbodiimide (DCC), optionally in the presence of 1-hydroxybenzotriazole (HOBT), and a base such as N,N-diisopropylethylamine, triethylamine, N-methylmorpholine, and the like. The reaction is typically carried out at 20 to 30° C., preferably at about 25° C., and requires 2 to 24 h to complete. Suitable reaction solvents are inert organic solvents such as halogenated organic solvents (e.g., methylene chloride, chloroform, and the like), acetonitrile, N,N-dimethylformamide, ethereal solvents such as tetrahydrofuran, dioxane, and the like.

Alternatively, the above elongation coupling step can be carried out by first converting the P3/P2 building block into an active acid derivative such as succinimide ester and then reacting it with the P1 amine. The reaction typically requires 2 to 3 h to complete. The conditions utilized in this reaction depend on the nature of the active acid derivative. For example, if it is an acid chloride derivative, the reaction is carried out in the presence of a suitable base (e.g. triethylamine, diisopropylethylamine, pyridine, and the like). Suitable reaction solvents are polar organic solvents such as acetonitrile, N,N-dimethylformamide, dichloromethane, or any suitable mixtures thereof.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in Greene, "Protective Groups in Organic Synthesis" (John Wiley & Sons, New York, 1981), which is hereby incorporated by reference. N-protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl, and the like, carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butoxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl, and the like; alkyl groups such as benzyl, triphenylmethyl, benzyloxymethyl and the like; and silyl groups such as trimethylsilyl and the like. Favoured N-protecting groups include formyl, acetyl, benzoyl, pivaloyl, t-butylacetyl, phenylsulfonyl, benzyl (bz), t-butoxycarbonyl (BOC) and benzyloxycarbonyl (Cbz).

Hydroxy and/or carboxy protecting groups are also extensively reviewed in Greene ibid and include ethers such as methyl, substituted methyl ethers such as methoxymethyl, methylthiomethyl, benzyloxymethyl, t-butoxymethyl, 2-methoxyethoxymethyl and the like, silyl ethers such as trimethylsilyl (TMS), t-butyldimethylsilyl (TBDMS) tribenzylsilyl, triphenylsilyl, t-butyldiphenylsilyl triisopropyl silyl and the like, substituted ethyl ethers such as 1-ethoxymethyl, 1-methyl-1-methoxyethyl, t-butyl, allyl, benzyl, p-methoxybenzyl, dipehenylmethyl, triphenylmethyl and the like, aralkyl groups such as trityl, and pixyl (9-hydroxy-9-phenylxanthene derivatives, especially the chloride). Ester hydroxy protecting groups include esters such as formate, benzylformate, chloroacetate, methoxyacetate, phenoxyacetate, pivaloate, adamantoate, mesitoate, benzoate and the like. Carbonate hydroxy protecting groups include methyl vinyl, allyl, cinnamyl, benzyl and the like.

DETAILED DESCRIPTION OF THE EMBODIMENTS

Various embodiments of the invention will now be described by way of illustration only with reference to the following Examples.

In the examples below, the following systems are typically employed:

Nuclear Magnetic Resonance (NMR) spectra were recorded on a Varian Gemini 7 Tesla 300 MHz instrument, or a Bruker Avance 400 MHz instrument in the solvent indicated. Chemical shifts are given in ppm down- and upfield from tetramethylsilane (TMS). Resonance multiplicities are denoted s, d, t, m, br and app for singlet, doublet, triplet, multiplet, broad and apparent, respectively. The Mass Spectrometry (MS) spectra were recorded on a Finnigan SSQ7000 TSP or a Finnigan SSQ710 DI/EI instrument. LC-MS was obtained with a Waters 2790 LC-system equipped with a Waters Xterra™ MS $C_8$ 2.5 μm 2.1×30 mm column, a Waters 996 Photodiode Array Detector and a Micromass ZMD. High pressure liquid chromatography (HPLC) assays were performed using a Hewlett Packard 1100 Series HPLC system equipped with a Zorbax column SB-$C_8$ 4.6 mm×15 cm. Column chromatography was performed using silica gel 60 (230-400 mesh ASTM, Merck) and thin layer chromatography (TLC) was performed on TLC precoated plates, silica gel 60 $F_{254}$ (Merck).

Preparation of Building Block 1, a P1 Building Block

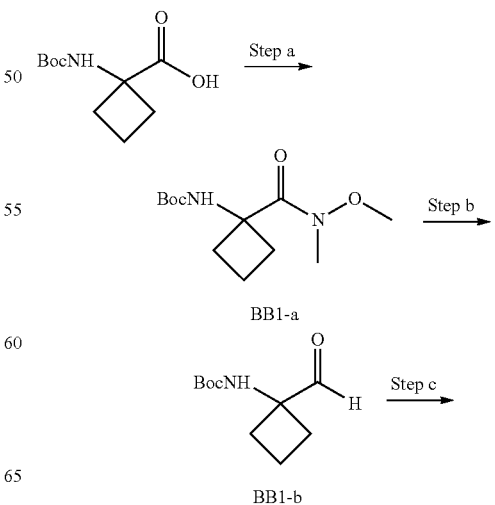

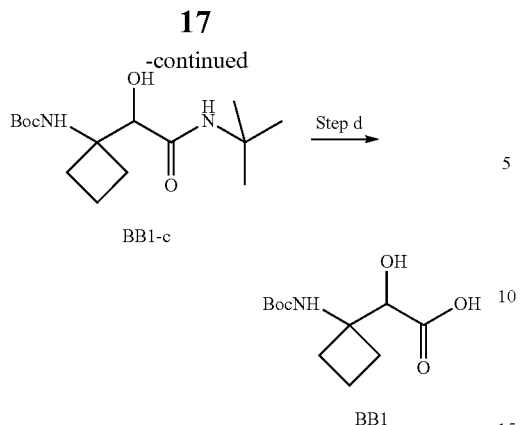

Step a) [1-(Methoxy-methyl-carbamoyl)-cyclobutyl]-carbamic acid tert-butyl ester (BB1-a)

To a solution of 1-tert-butoxycarbonylamino-cyclobutanecarboxylic acid (3 g, 13.94 mmol) in dry DMF (50 mL) was added N,O-dimethylhydroxylamine×HCl (1.36 g, 13.94 mmol) and DIEA (9.21 mL, 55.75 mmol). The reaction flask was cooled to 0° C. and after 10 minutes HATU (5.30 g, 13.94 mmol) was added to the solution (which turned yellow on addition). After 2 hrs the DMF was removed by rotary evaporation at reduced pressure. The residue was dissolved in EtOAc (100 mL) and washed twice with 10% citric acid (aq) and saturated NaHCO$_3$(aq) solution. The organic phase was dried with Na$_2$SO$_4$, filtered and evaporated on silica. The product was purified by flash chromatography (heptane: ethyl acetate (1:1) to give the product as a colourless oil that slowly crystallizes (3.13 g) in 87% yield.

Step b) (1-Formyl-cyclobutyl)-carbamic acid tert-butyl ester (BB1-b)

LiAlH$_4$ (202 mg, 5.33 mmol) was added to a solution of the Weinreb amide BB1-a (1.10 g, 4.27 mmol) dissolved in dry diethyl ether (35 mL) at 0° C. The solution was stirred at 15 minutes before the reaction was quenched with slow addition of potassium hydrogen tartaric acid (sat, aq) and stirred for 10 minutes. The solution was poured into a separatory funnel and the water phase was extracted with ethyl acetate twice. The combined organic phases were washed with 0.5 M HCl (3 times), NaHCO$_3$(aq) (2 times) and brine (1 time). The organic phase was dried with Na$_2$SO$_4$, filtered and evaporated on silica. The product was purified by flash chromatography (heptane: ethyl acetate (4:1→3:1) to give the product as white crystals (0.647 g) in 76% yield.

Step c) [1-(tert-Butylcarbamoyl-hydroxy-methyl)-cyclobutyl]-carbamic acid tert-butyl ester (BB1-c)

BB1-b, (1.75 g, 8.78 mmol) was dissolved in CH$_2$Cl$_2$ (18 mL) and cooled in an ice bath, under inert gas. Pyridine (2.85 mL) was added, followed by t-butyl isocyanide (1.50 mL, 13.3 mmol). Trifluoroacetic acid (1.35 mL, 17.5 mmol) was then added dropwise over 30 min. The yellow solution was stirred at RT overnight. The mixture was concentrated, diluted with EtOAc (100 mL) and washed successively with 1N HCl (50 mL), saturated NaHCO$_3$ (50 mL) and saturated NaCl (2×50 mL). Drying (Na$_2$SO$_4$) and concentration under vacuum. The afforded crude product was treated with THF (2.5 mL) and 1M LiOH in 3/1 MeOH-water (2.5 mL) at RT. TLC (3/1 petroleum ether—EtOAc) showed complete ester hydrolysis after 15 min. After 45 min reaction time, 1N HCl (2.5 mL), water (10 mL) and EtOAc (20 mL) were added, and the layers were separated. The organic phase was washed with saturated NaHCO$_3$ (20 mL) and then saturated NaCl (2×20 mL), dried (Na$_2$SO$_4$) and concentrated. Flash chromatography (75 g silica, 5/1 to 1/1 petroleum ether—EtOAc) gave a white solid (2.36 g, 89%).

Step d (1-Tert-butoxycarbonylamino-cyclobutyl)-hydroxyacetic acid (BB1)

BB1-c (1.30 g, 4.33 mmol) was refluxed with 6N HCl (40 mL) until amide hydrolysis was complete as monitored by LCMS. The mixture was evaporated, co-evaporating several times with water. 1M NaOH (15 mL) was added to the residue and the basic solution was stirred under vacuum for 15 min. Boc$_2$O (1.92 g, 8.80 mmol) in dioxane (10 mL) was added, keeping pH at 10-11, and the mixture was stirred at RT overnight. The mixture was diluted with water (50 mL), acidified with 1N HCl to pH 3, in an ice bath, and then extracted with EtOAc (2×50 mL, then 30 mL). The organic phase was washed with saturated NaCl (50 mL), dried (Na$_2$SO$_4$) and evaporated to give crude P1 building block BB1 (0.649 g).
$^1H$NMR (400 MHz, d$_6$-DMSO) δ 6.88 (br s, 1H), 4.15 (s, 1H), 2.40 (br m, 2H), 1.98 (br m, 2H), 1.80 (br m, 2H), 1.35 (s, 9H); ms ES$^+$ m/z 146 (100%), 190 (50%).

Preparation of Building Block 2, a P1 Building Block

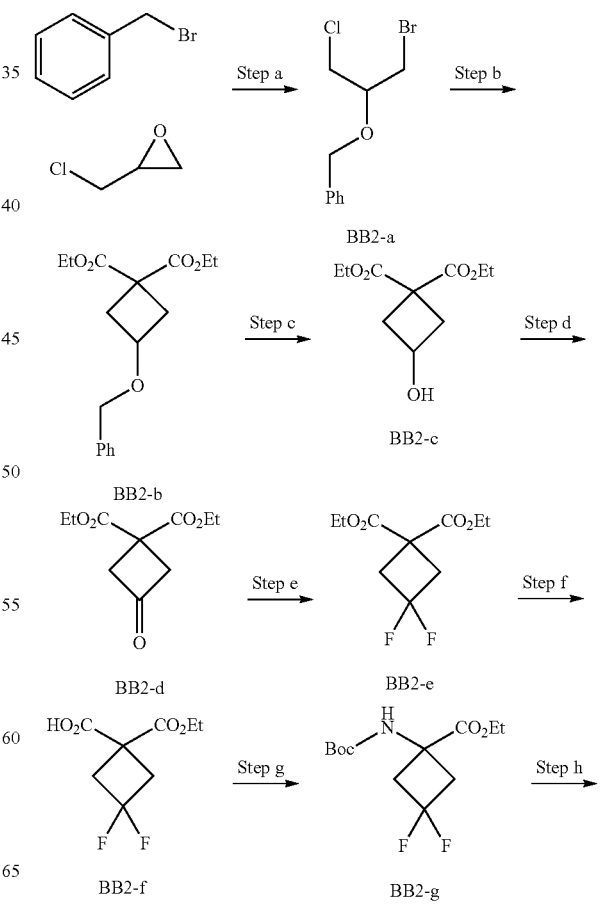

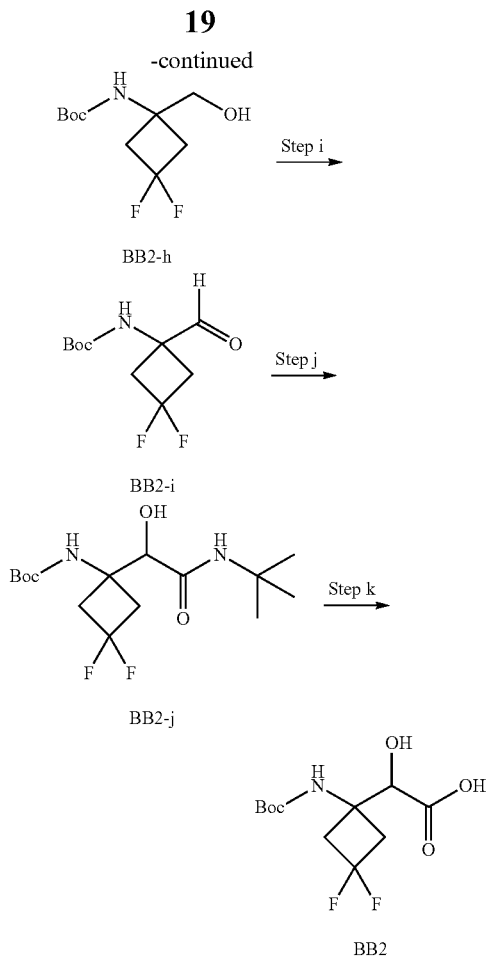

-continued

BB2-h

BB2-i

BB2-j

BB2

Step a) ((1-Bromo-3-chloropropan-2-yloxy)methyl)benzene (BB2-a)

To a stirred mixture of benzyl bromide (185 g, 1.08 mol) and (1.5 g) of mercurous chloride was added epichlorohydrin (100 g, 1.08 mol). The reaction mixture was heated for 12 hr at 100° C. TLC analysis confirmed formation of product. The product was separated from the dark brown reaction mixture by column chromatography using petroleum ether as eluent. TLC system; Petroleum ether: ethyl acetate (9:1), $R_F$=0.7. Yield; 148 g, 51%.

Step b) 3-Benzyloxy-cyclobutane-1,1-dicarboxylic acid diethyl ester (BB2-b)

To a stirred suspension of sodium hydride (22.5 g, 0.562 mol) in 800 mL of dry dioxane, was added diethyl malonate (90 g, 0.562 mol) drop-wise over 20 min. After this addition was complete, BB2-a (148 g, 0.56 mol) was added drop-wise over 20 min. The mixture was then heated at reflux for 24 hr. After cooling to room temperature, sodium hydride (22.5 g, 0.562 mol) in a little dioxane (~20 mL) was added to the mixture and heating at reflux was continued for an additional 48 hr. The solvent was partially removed under reduced pressure and the mixture was treated with 800 mL of water. This mixture was then extracted with ethyl acetate (500 mL×3), extracts were dried ($Na_2SO_4$) and concentrated in vacuo and the residue was purified by column chromatography using petroleum ether: ethyl acetate (10%) which gave the title compound. TLC system; petroleum ether: ethyl acetate (9:1), $R_F$=0.3. Yield: 100 g, 58%

Step c) Diethyl 3-hydroxycyclobutane-1,1-dicarboxylate (BB2-c)

To a solution of compound BB2-b (40 g) in EtOH (500 mL) was added 10% palladium on charcoal (4 g) and the mixture was hydrogenated for 3.5 hours at 50 psi at room temperature. The catalyst was removed by filtration, washed with ethyl acetate, EtOH and the solvent was then removed under reduced pressure. The residue was purified by silica gel chromatography with hexane/ethyl acetate as eluent to provide the title compound. TLC system; Petroleum ether: ethyl acetate (9:1), $R_F$=0.3. Yield: 18 g, 64%.

Step d) Diethyl 3-oxocyclobutane-1,1-dicarboxylate (BB2-d)

To a solution of compound BB2-c (18 g, 0.0833 mol) in DCM (200 mL) was added PCC (37 g, 0.176 mol) and the mixture was stirred for four hours at room temperature. The solution was filtered through a silica gel column and the residue was washed with DCM/MeOH 98/2 and then filtered through a similar column. The combined fractions were evaporated under reduced pressure to provide the desired compound. TLC system; Petroleum ether: ethyl acetate (9:1), $R_F$=0.3. Yield: 11 g, 62%.

Step e) Diethyl 3,3-difluorocyclobutane-1,1-dicarboxylate (BB2-e)

To a cooled solution of compound BB2-d (11 g, 0.0513 mol) in dry DCM (150 mL) was added drop-wise a solution of DAST (18.72 g, 0.116 mol) and the mixture was stirred at room temperature overnight. The mixture was added to ice water and was extracted three times with DCM. The solution was dried with sodium sulphate and evaporated under reduced pressure. The residue was purified by silica gel chromatography employing hexane/ethyl acetate as eluent to provide the title compound. TLC system; Petroleum ether: ethyl acetate (7:3), $R_F$=0.5. Yield: 7.7 g, 64%.

Step f) 1-(Ethoxycarbonyl)-3,3-difluorocyclobutanecarboxylic acid (BB2-f)

Compound BB2-e (7.7 g, 0.0325 mol) was dissolved in ice cooled 0.5 M ethanolic potassium hydroxide solution (30 mL) and water (6 mL). The mixture was stirred at room temperature overnight. Water was added and most of the ethanol was removed under reduced pressure. The mixture was acidified with 2M HCl and extracted three times with ethyl acetate. The organic phase was dried with sodium sulphate and evaporated under reduced pressure to give the desired compound. TLC system: petroleum ether: ethyl acetate (1:1), $R_F$=0.3. Yield: 5.8 g, 86%.

Step g) Ethyl 1-(tert-butoxycarbonylamino)-3,3-difluorocyclobutanecarboxylate (BB2-g)

To a solution of compound BB2-f (5.8 g, 0.0273 mol) in dry dioxane (100 mL) was added tert-butanol (24.4 mL), DPPA (7.87 g, 0.027 mol) and TEA (2.87 g, 0.0284 mol) and the mixture was refluxed for five hours. Ethyl acetate (about 200 mL) was added and the organic phase was washed twice with 5% citric acid and saturated sodium hydrogen carbonate. The solution was dried and evaporated under reduced pressure. The desired product was isolated by silica gel chromatography with hexane/ethyl acetate. TLC system; Petroleum ether: ethyl acetate (1:1), $R_F$=0.5. Yield: 4 g, 51.4%.

Step h) tert-Butyl 3,3-difluoro-1-(hydroxymethyl)cyclobutylcarbamate (BB2-h)

To a ice cooled solution of compound BB2-g (4 g, 0.0143 mol) in dry THF (100 mL) was slowly added a solution of 2M lithium borohydride (30 mL) and the mixture was allowed to warm up to room temperature. The mixture was stirred for three hours at room temperature. Ice water and 5% citric acid were added and the mixture was extracted three times with DCM. The organic phase was dried (Na$_2$SO$_4$), filtered and evaporated under reduced pressure which gave the title compound. TLC system petroleum ether: ethyl acetate (1:1), $R_F$=0.3. Yield: 3.1 g, 91%.

Step i) tert-Butyl 3,3-difluoro-1-formylcyclobutylcarbamate (BB2-i)

To a solution of compound BB2-h (3.1 g, 0.0130 mol) in dry DCM (100 mL) was added Dess
Martin Period inane (19.9 g, 0.0470 mol) and the mixture was stirred for three hours at room temperature. Ethyl acetate (200 mL) was added and the organic phase was washed twice with 10% sodium thiosulphate solution, twice with 0.5 M NaOH and with brine. The organic phase was dried and evaporated under reduced pressure. The residue was purified by silica gel chromatography with hexane/ethyl acetate as eluent which gave the title compound. TLC system; petroleum ether: ethyl acetate (1:1), $R_F$=0.4. Yield: 2.7 g, 87%.

Step j) tert-Butyl 1-(2-(tert-butylamino)-1-hydroxy-2-oxoethyl)-3,3-difluorocyclobutylcarbamate (BB2-j)

To a ice cooled solution of compound BB2-i (1.5 g, 0.0064 mol) in dry DCM (100 mL) was added tert-butylisocyanate (0.81 g, 0.009 mol) and pyridine (2.04 g, 0.027 mol). Trifluoroacetic acid (1.58 g, 0.015 mol) was added over a ten minutes period. The mixture was stirred for five hours at room temperature. Ethyl acetate was added and the organic phase was washed twice with 5% citric acid and brine. The organic phase was evaporated and dissolved in dioxane (50 mL). 1M LiOH solution (100 mL) was added and the mixture was stirred overnight at room temperature. 5% Citric acid was added and the mixture was extracted three times with ethyl acetate. The organic phase was washed with brine, dried (Na$_2$SO$_4$), filtered and evaporated under reduced pressure. The product was purified by silica gel chromatography with hexane/ethyl acetate as eluent. TLC system; Petroleum ether: ethyl acetate (1:1), $R_F$=0.4. Yield: 1.0 g, 46%.

Step k) 2-(1-(Tert-Butoxycarbonylamino)-3,3-difluorocyclobutyl)-2-hydroxyacetic acid (BB2)

Compound BB2-j (1 g) was dissolved in 6N HCl (40 mL), and heated to reflux for 24 h after which TLC showed that the reaction had reached completion. The reaction mixture was concentrated in vacuo and residue was dissolved in THF; H$_2$O (7; 3, 50 mL), and TEA (1.8 mL, 0.012 mol) and Boc anhydride (2.6 g, 0.012 mol) were both added. The mixture was stirred at RT for 8 h when TLC confirmed the reaction had reached completion. The reaction mixture was concentrated in vacuo and the residue was purified by column chromatography using 5% methanol in chloroform which gave the title compound. TLC system; MeOH: CHCl$_3$ (1:9), $R_F$=0.4. Yield: 0.6 g, 72%.

$^{1H}$ NMR (400 MHz, d$_6$-DMSO) δ 7.30 (br s, 1H), 4.11 (s, 1H), 2.90 (br m, 2H), 2.61 (br m, 2H), 1.35 (s, 9H); ms ES$^+$ m/z 281 (100%).

Preparation of Building Block 3—a P1 Building Block

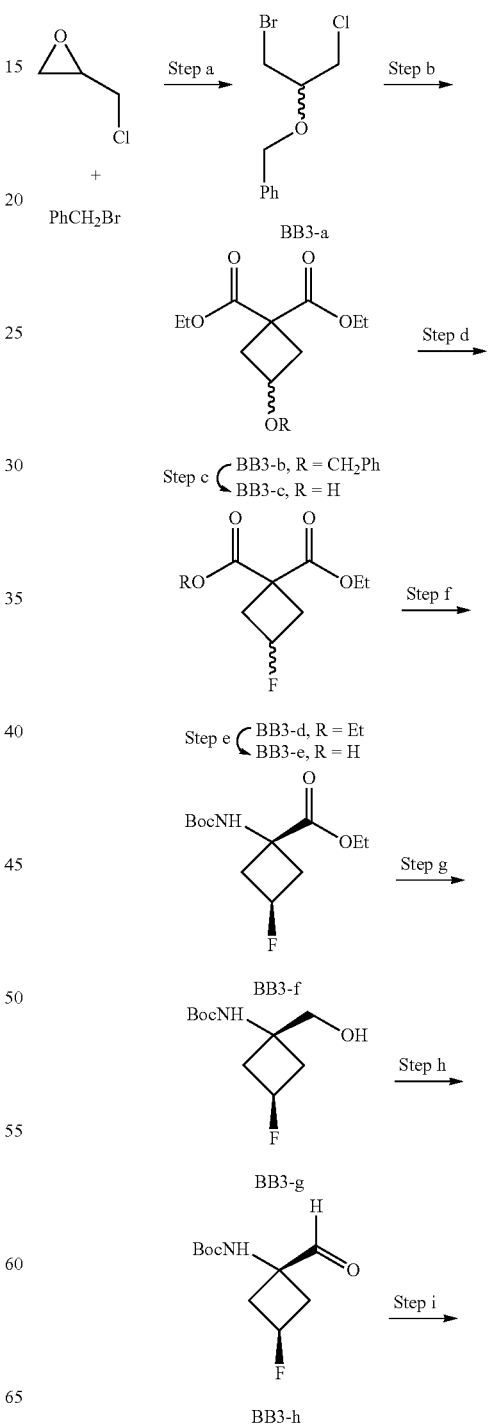

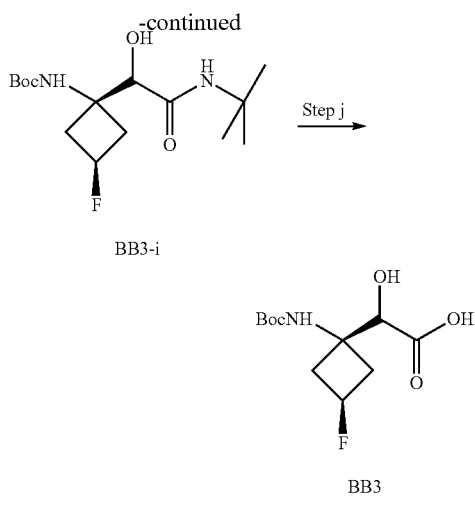

BB3-i

BB3

Step a) ((1-Bromo-3-chloropropan-2-yloxy)methyl) benzene (BB3-a)

A mixture of benzyl bromide (46.0 g, 0.269 mol) and epichlorohydrin (24.9 g, 0.269 mol) and mercurous chloride (0.04 g, 0.085 mmol) was heated for 12 h at 150° C. The crude product was purified by column chromatography (silica gel 60-120 mesh, eluent 1% EtOAc in pet ether) which afforded the title compound as a viscous liquid (50 g, yield 70%). TLC system: 10% EtOAc in pet ether, $R_f$=0.6.

Step b) Diethyl 3-(benzyloxy)cyclobutane-1,1-dicarboxylate (BB3-b)

In a three-neck flask equipped with stirrer, additional funnel and reflux condenser was place NaH (4.6 g, 0.192 mol) in dry dioxane (150 mL). To this stirred reaction mixture, diethyl malonate (30.75 g, 0.192 mol) was added drop-wise over 30 min. After the addition was complete, compound BB3-a (50 g, 0.19 mol) was added drop-wise over a period of 30 min. The reaction mixture was refluxed for 24 h. After cooling to room temperature, NaH (4.6 g, 0.192 mol) and dry dioxane (40 mL) was added to the reaction mixture and further heated to reflux for another 48 h. The solvent was partially removed under reduced pressure and the mixture was treated with water (150 mL). The product was extracted with diethyl ether (3×100 mL), the organic layer was washed with brine and dried over anhydrous $Na_2SO_4$. Solvent was concentrated in vacuum and the crude product was purified by column chromatography (silica gel 60-120 mesh, eluent 2% EtOAc in pet ether) which afforded the title compound as a viscous liquid (33 g, yield 57%). TLC system: 15% EtOAc in pet ether, $R_f$=0.5.

Step c) Diethyl 3-hydroxycyclobutane-1,1-dicarboxylate (BB3-c)

To a solution of compound BB3-b (33 g, 0.108 mol) in EtOH (300 mL) was added 10% palladium on charcoal (10 g) and the mixture was hydrogenated for 48 h with 50 psi pressure at room temperature. The catalyst was removed by filtration through a celite bed and washed thoroughly with EtOAc. The solvent was removed under reduced pressure. The product was purified by silica gel chromatography (silica gel 60-120 mesh, eluent 20% EtOAc in pet ether) which afforded the title compound as a viscous liquid (12 g, yield 51%). TLC system: 30% EtOAc in pet ether, $R_f$=0.3.

Step d) Diethyl 3-fluorocyclobutane-1,1-dicarboxylate (BB3-d)

Compound BB3-c (0.8 g, 0.0037 mol) was dissolved in dry DCM (16 mL) and cooled to 0° C. DAST (1.8 g, 0.011 mol) was added drop-wise to the cold solution. The reaction mixture was warmed to room temperature stirred for 12 h. The reaction mixture was quenched with cold saturated $NaHCO_3$ solution. The crude product was extracted with DCM (100 mL). The organic layer was washed with 10% $NaHCO_3$ solution, water followed by brine and dried over anhydrous $Na_2SO_4$. Solvent was concentrated in vacuum and the crude product was purified by column chromatography (silica gel 60-120 mesh, eluent 1-2% EtOAc in pet ether) which afforded the title compound as a pale yellow liquid (460 mg, yield 57%). TLC system: 10% EtOAc in pet ether, $R_f$=0.4.

Step e) 1-(Ethoxycarbonyl)-3-fluorocyclobutanecarboxylic acid (BB3-e)

Compound BB3-d (0.46 g, 0.0021 mol) was dissolved in ice cooled 0.5M potassium hydroxide solution in EtOH (4.2 mL) and water (1.4 mL). The mixture was stirred at room temperature overnight. Water was added and most of the ethanol was removed under reduced pressure. The mixture was acidified with 2N HCl and extracted with EtOAc (3×50 mL). The organic phase was dried over anhydrous $Na_2SO_4$. Solvent was concentrated in vacuum to afford the crude title compound (0.35 g, crude) which was used as such for the next step. TLC system: 50% EtOAc in pet ether, $R_f$=0.3.

Step f) Ethyl 1-(tert-butoxycarbonylamino)-3-fluorocyclobutanecarboxylate (BB3-f)

To a solution of compound BB3-e (0.35 g, 0.0018 mol) in dry dioxane (6 mL) was added tert-butanol (1.8 mL), diphenyl phosphoryl azide (0.56 g, 0.002 mol) and triethylamine (0.2 g, 0.002 mol) and the mixture was refluxed for 5 h. After completion of the reaction, EtOAc (60 mL) was added to the reaction mixture and the organic layer was washed with 5% citric acid (2×20 mL) followed by saturated $NaHCO_3$ (50 mL). The organic solvent was evaporated under reduced pressure. To the residue EtOAc (100 mL) was added and the organic layer was washed with brine and dried over anhydrous $Na_2SO_4$. Solvent was concentrated in vacuum and the crude product was purified by column chromatography (silica gel 60-120 mesh, eluent 5-10% EtOAc in pet ether) which afforded the title compound as white crystals (0.27 g, yield 56%). TLC system: 20% EtOAc in pet ether, $R_f$=0.4.

Step g) tert-Butyl 3-fluoro-1-(hydroxymethyl)cyclobutylcarbamate (BB3-g)

To a ice cooled solution of compound BB3-f (0.27 g, 0.001 mol) in dry THF (10 mL) was slowly added a solution of 2M lithium borohydride (2 mL, 0.004 mol) and the mixture was allowed to warm up to room temperature. The mixture was stirred for 3 h at room temperature. The reaction mixture was quenched with ice water (2 mL) and 5% citric acid (5 mL) and the crude product was extracted with DCM (2×50 mL). The organic layer was washed with brine and dried over anhydrous $Na_2SO_4$. Solvent was concentrated in vacuum and the crude product was purified by column chromatography (silica gel 60-120 mesh, eluent 15-18% EtOAc in pet ether) which afforded the title compound as white solid (90 mg, yield 39%). TLC system: 50% EtOAc in pet ether, $R_f$=0.5.

Step h) tert-Butyl 3-fluoro-1-formylcyclobutylcarbamate (BB3-h)

To a degassed solution of compound BB3-g (90 mg, 0.0004 mol) in dry DCM (4.5 mL) was added Dess-Martin Periodinane (0.21 g, 0.0005 mol) and the mixture was stirred for 3 h at room temperature. EtOAc (30 mL) was added and the organic layer was washed with 10% sodium thiosulphate solution (2×10 mL), 0.5 M NaOH (20 mL) and with brine. The organic layer was dried over anhydrous $Na_2SO_4$. Solvent was concentrated in vacuum and the crude product was purified by column chromatography (silica gel 60-120 mesh, eluent 10-15% EtOAc in pet ether) which afforded the title compound as a white crystalline solid (75 mg, yield 87%). TLC system: 20% EtOAc in pet ether, $R_f$=0.4.

Step i) tert-Butyl 1-(2-(tert-butylamino)-1-hydroxy-2-oxoethyl)-3-fluorocyclobutylcarbamate (BB3-i)

To an ice cooled solution of compound BB3-h (1.3 g, 0.0059 mol) in dry DCM (25 mL) was added tert-butyl isocyanide (0.75 g, 0.0089 mol) and dry pyridine (2.6 mL). Trifluoroacetic acid (0.9 mL, 0.0118 mol) was added over a period of ten minutes maintaining the temperature at 0° C. The reaction mixture was slowly warmed to room temperature and stirred for 16 h. EtOAc (50 mL) was added and the organic phase was washed twice with 5% citric acid and brine. The organic phase was evaporated and the crude product was dissolved in THF (25 mL). 1M LiOH solution in MeOH—$H_2O$ (3:2 v/v) (2.6 mL) was added and the mixture was stirred for 2 h at room temperature. The reaction mixture was quenched with 5% citric acid and the mixture was extracted with ethyl acetate (2×25 mL). The organic layer was washed with brine and dried over anhydrous $Na_2SO_4$. Solvent was evaporated in vacuum and to afford the title compound which was pure enough to be used in the next step (1.6 g, yield 84%). TLC system: 20% EtOAc in pet ether, $R_f$=0.3.

Step j) 2-(1-(tert-Butoxycarbonylamino)-3-fluorocyclobutyl)-2-hydroxyacetic acid (BB3)

Compound BB3-i (1.6 g, 0.005 mol) was refluxed with 6N HCl (60 mL) for 16 h until the amide hydrolysis was complete. The solvent was evaporated under reduced pressure and co-evaporated several times with water. The product was dissolved in THF:$H_2O$ (7:3 v/v, 50 mL), cooled to 0° C. and $Et_3N$ (2.1 mL, 0.015 mol) was added followed by di-tert-butyl dicarbonate (2.18 g, 0.01 mol). The mixture was stirred at room temperature overnight (pH was monitored in a regular interval and kept ~11 throughout the reaction). The reaction mixture was neutralized with 1N HCl and the product was extracted with EtOAc (2×50 mL). The organic layer was washed with brine and dried over anhydrous $Na_2SO_4$. The solvent was evaporated under reduced pressure followed by purification by column chromatography (silica gel 60-120 mesh, eluent 5% MeOH in $CHCl_3$) which afforded the title P1 building block as a solid (0.65 g, yield 50%). TLC system: 30% MeOH in $CHCl_3$, $R_f$=0.3.

$^1$H NMR (400 MHz, $d_6$-DMSO) δ 7.01 (br s, 1H), 5.16 (br m, 1H), 4.97 (br m, 1H), 2.49 (br m, 5H), 1.36 (s, 9H); ms ES$^+$ m/z 262 (100%).

Building Block 4—a P1-Prime Side Building Block

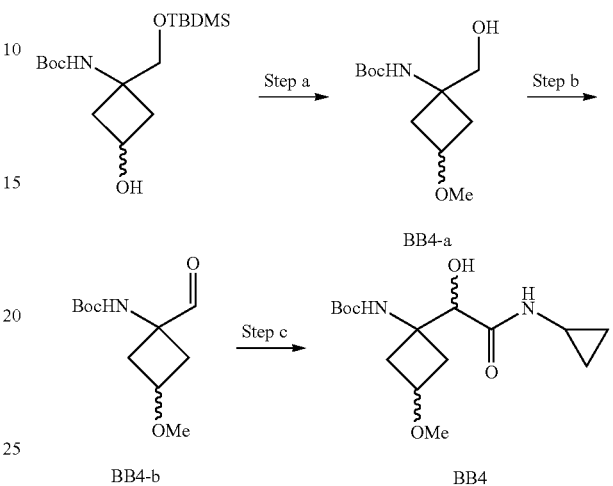

Step a) tert-butyl 1-(hydroxymethyl)-3-methoxycyclobutylcarbamate (BB4-a)

500 mg (1.51 mmol) of tert-butyl 1-((tert-butyldimethylsilyloxy)methyl)-3-hydroxycyclobutylcarbamate (prepared by reduction of ethyl-1[[(tert-butyloxy)carbonyl]amino]-3-hydroxycyclobutane-1-carboxylate as described in J. Med. Chem., 1990 33(10) 2905-2915) and proton sponge (N,N,N', N' tetramethylnapthalene-1,8 diamine) (1.63 g, 6.04 mmol) were dissolved in DCM (18 mL), cooled down to 0° C., and 447 mg (3.02 mmol) of trimethyloxonium borontetrafluoride was added in one portion as a solid under vigorous stirring. The reaction mixture was stirred for 3 h and diluted with DCM (50 mL) and brine (20 mL), added under vigorous stirring. The organic phase was washed with sodium bicarbonate, brine, dried over sodium sulphate, evaporated and purified on short silica column (DCM as an eluent). The resulting product was dissolved in THF (5 mL), and a solution of tetrabutylammonium fluoride in THF (1M, 4.5 mL) was added, and the reaction was stirred at room temperature for 4.5 h. The reaction was monitored by TLC and once deemed to have reached completion, it was absorbed onto silica and purified on silica (EtOAc-hexane 1:1 to neat EtOAc) to give the title compound (251 mg, 72%). LC/MS 232 (M+1).

Step b) tert-Butyl 1-formyl-3-methoxycyclobutylcarbamate (BB4-b)

Alcohol BB4-a was dissolved in DCM (20 mL) and Dess-Martin reagent was added in one portion. The reaction was stirred for 2.5 hours. Once the reaction was deemed to have reached completion, it was diluted with 50 mL of DCM and 20 mL of 10% $Na_2S_2O_3$ was added. The mixture was stirred, washed with sodium bicarbonate, brine, and the organic phase was dried over sodium sulphate. Purification on silica (EtOAc-hexane 1:1 to neat EtOAc) gave the title compound (500 mg, 59%).

Step c) tert-Butyl 1-(2-(cyclopropylamino)-1-hydroxy-2-oxoethyl)-3-methoxycyclobutylcarbamate (BB4)

Aldehyde BB4-b 498 mg (1.56 mmol) was dissolved in dry DCM (8 mL). Pyridine (0.52 mL) was added under stirring conditions, followed by adding cyclopropyl isonitrile. The reaction was placed in an ice-bath and TFA (0.25 mL) was added dropwise during 20 min. The reaction mixture was stirred overnight. The reaction was then deemed to have reached completion and was washed with 1 M HCl, sodium bicarbonate, brine, and the organic phase was dried over sodium sulphate and evaporated. The remaining residue was dissolved in dioxane and stirred with lithium hydroxide solution overnight and then neutralized with citric acid. The product was extracted with EtOAc from the resulting solution and purified on silica (EtOAc-hexane 1:3 to 1:1) which gave 263 mg of the title compound (54%) LC/MS 314 (M+1).

Building Block 5 (BB5)—a P2 Building Block

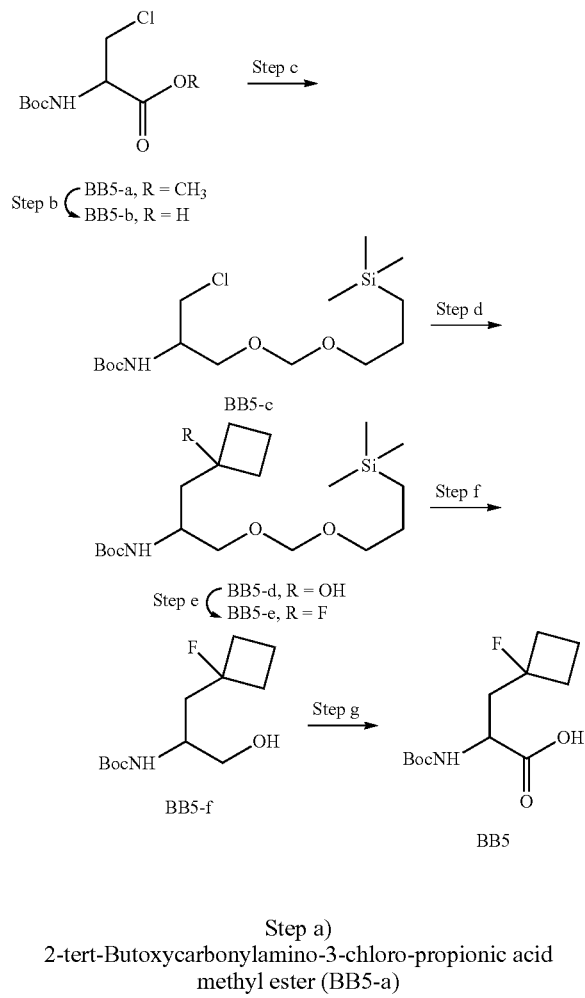

Step a) 2-tert-Butoxycarbonylamino-3-chloro-propionic acid methyl ester (BB5-a)

A solution of triphenylphosphine (65.8 g, 0.251 mol)) and hexachloroethane (59.4 g, 0.251 mol) in dichloromethane (850 mL) was added in one portion to a solution of N-Boc-serine methyl ester (50 g, 0.228 mol) in dichloromethane (170 mL) under argon atmosphere. The reaction mixture was stirred at room temperature for 2 h and then the reaction was quenched with a saturated solution of NaHCO$_3$ (150 mL). The organic product was extracted with dichloromethane (2×300 mL) and the combined organic layers was washed with brine (300 mL) and dried over anhydrous sodium sulphate. The solution was concentrated under reduced pressure and then triturated with Et$_2$O (500 mL). After filtration and evaporation of the solvent, the crude product was purified by chromatography on a silica column eluted with 6-8% EtOAc in pet ether) which gave the title compound (42 g, 78%).

Step b) (2-Chloro-1-hydroxymethyl-ethyl)-carbamic acid tert-butyl ester (BB5-b)

Lithium borohydride (4.3 g, 0.195 mol) was added in portions to a stirred solution of BB5-a (42 g, 0.177 mol) in EtOH-THF 9:1 at 0° C. under argon atmosphere. The reaction was stirred for 8 h at room temperature then quenched with a saturated solution of ammonium chloride (20 mL).

The product was extracted with EtOAc (2×300 mL). The combined organic layers was washed with brine (300 mL) and dried over anhydrous sodium sulphate. The solvent was evaporated under reduced pressure and the afforded crude product was purified by chromatography on a silica column eluted with 15% EtOAc in pet ether, which gave the title compound (27.5 g, 74%).

Step c) [2-Chloro-1-(2-trimethylsilanyl-ethoxymethoxymethyl)-ethyl]-carbamic acid tert-butyl ester (BB5-c)

(2-Chloromethoxy-ethyl)-trimethyl-silane (26.18 g, 0.157 mol) was added drop-wise to a stirred solution of compound BB5-b (27.5 g, 0.131 mol) and N,N-diisopropylethylamine (27.4 mL, 0.157 mol) in dichloromethane (350 mL) at 0° C. under argon atmosphere. The reaction was allowed to attain room temperature and stirred for 18 h. The reaction mixture was concentrated under vacuum and then diluted with EtOAc (150 mL). The product was extracted with EtOAc (2×200 mL) and the organic layer was washed with brine (100 mL) and dried over anhydrous sodium sulphate. The solvent was evaporated under reduced pressure and the afforded crude product was purified by chromatography on silica a column eluted with 5% EtOAc in pet ether, which gave the title compound (25.5 g, 57%).

Step d) [2-(1-Hydroxy-cyclobutyl)-1-(2-trimethylsilanyl-ethoxymethoxymethyl)-ethyl]-carbamic acid tert-butyl ester (BB5-d)

n-BuLi (10 mL, 0.016 mol, 1.6 M solution in hexanes) was added drop-wise to a stirred solution of compound BB5-c (2 g, 5.88 mmol) in THF (170 mL) at −78° C. under argon atmosphere. The stirring was continued for 15 min, followed by drop-wise addition of LiNp (104 mL, 0.42 M solution in THF, 0.044 mol) over 5 min. The dark solution was stirred at −78° C. for 1 h and then cyclobutanone (0.88 mL, 11.77 mmol) was added drop-wise. The reaction mixture was stirred at −78° C. for 16 h then quenched with a saturated solution of NH$_4$Cl (50 mL) and allowed to warm to room temperature. The reaction was diluted with ether (100 mL) and a saturated solution of NH$_4$Cl (10 mL). The layers were separated and the aqueous layer was extracted with ether (2×100 mL). The combined organic layers was dried (Na$_2$SO$_4$) and the solvent was evaporated under reduced pressure. The crude product was purified by chromatography on a silica column eluted with heptane:ether 3:2, which gave the title compound (1.54 g, 70%).

Step e) [2-(1-Fluoro-cyclobutyl)-1-(2-trimethylsilanyl-ethoxymethoxymethyl)-ethyl]-carbamic acid tert-butyl ester (BB5-e)

BB5-d (0.5 g, 1.33 mmol), 50% Deoxofluor in THF (excess) and pyridine (excess) were mixed in DCM (10 mL). The resulting mixture was stirred at rt over night. The reaction mixture was washed with 10% citric acid (aq) and sat. NaHCO$_3$ (aq). The organic phase was dried (Na$_2$SO$_4$) and evaporated. The afforded crude product was purified by chromatography on a silica column using hexane:EtOAc (7:1 to 2:1) as eluent, which gave the title compound (192 mg, 38%).

Step f) [2-(1-Fluoro-cyclobutyl)-1-hydroxymethyl-ethyl]-carbamic acid tert-butyl ester (BB5-f)

A solution of BB5-e (192 mg, 0.51 mmol) in 0.1 M HCl in MeOH (20 mL) was stirred for 3 hours, then triethylamine (1 mL) was added and the solution was concentrated. The afforded crude product was purified by chromatography on a silica column using hexane:EtOAc (2:1) as eluent, which gave the title compound (69.3 mg, 55%) as a white solid.

Step g) 2-tert-Butoxycarbonylamino-3-(1-fluoro-cyclobutyl)-propionic acid (BB5)

BB5-f (69 mg, 0.279 mmol) and pyridine dichromate (1.15 g, 3.05 mmol) were dissolved in dry DMF (5 mL). After five hours H$_2$O (15 mL) was added and the product was extracted with DCM (3×20 mL). The combined organic layers was dried (Na$_2$SO$_4$) and evaporated. The crude was purified by chromatography on a silica column using hexane:EtOAc (1:1) followed by EtOH (100%) as eluent. This afforded the title compound as a white solid (22.3 mg, 31%), 262.4 [M+H]$^+$.

Building Block 6 (BB6)—a P1-Prime Side Building Block

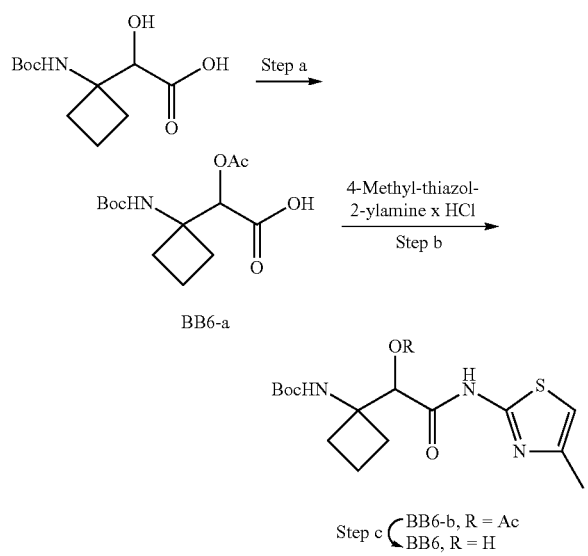

Step a) Acetoxy-(1-tert-butoxycarbonylamino-cyclobutyl)-acetic acid BB6-a (1-Tert-butoxycarbonylaminocyclobutyl)-hydroxyacetic acid (201.5 mg, 0.822 mmol) was stirred with acetic anhydride (95 mL) in pyridine (1.5 mL) for 24 h. The mixture was first concentrated under vacuum, and then diluted with 5 mL EtOAc. The organic solution was washed with 1N HCl (2 mL) followed by saturated aqueous NaCl (2 mL), dried (Na$_2$SO$_4$), and evaporated under vacuum which gave the title compound. LC-UV/MS API-ES– m/z 286 [M–H]$^-$ $^1$H NMR (400 MHz, DMSO-d6) δ ppm 7.11 (s, 1H), 5.00 (s, 1H, CHOAc), 2.28 (m, 2H), 2.07 (s, 3H, Me), 2.04 (m, 2H), 1.81 (m, 1H), 1.67 (m, 1H), 1.35 (s, 9H, Boc).

Step b) Acetic acid (1-tert-butoxycarbonylamino-cyclobutyl)-(4-methyl-thiazol-2-ylcarbamoyl)-methyl ester (BB6-b)

A mixture of the α-acetoxy carboxylic acid BB6-a (0.23 mmol) and 1,1'-carbodiimidazole (87 mg, 0.54 mmol) in dry THF (5.6 mL) was stirred at rt. After 18 h, 4-methyl-2-aminothiazole hydrochloride (0.28 mmol), imidazole (20 mg, 0.29 mmol), and DMAP (0.5 mg) were added and stirring was continued at rt. After 26 h, very little amide was formed, so the mixture was heated at 65° C. for 4 h, and then concentrated under vacuum. The residue was partitioned between 10 mL EtOAc and 10 mL saturated aqueous NaCl. The aqueous phase was extracted further with EtOAc (2×10 mL). The organic phases were combined, dried (Na$_2$SO$_4$), and evaporated in vacuo to give 152 mg oil as crude material. Flash column chromatography (silica, 80/20 CH$_2$Cl$_2$-acetone) gave the title compound as white solids (62.8 mg, 71% yield).

TLC Rf (9/1 CH$_2$Cl$_2$-acetone) 0.70, LC-UV/MS 97% DAD, API-ES+ m/z 384 [M+H]$^+$ $^1$H NMR (400 MHz, DMSO-d6) δ ppm 6.95 (s, 1H), 6.76 (s, 1H, thiazole), 5.16 (s, 1H, CHOAc), 2.26 (s, 3H, thiazole Me), 2.14 (s, 3H, Ac), 2.4-2.1 (m, 4H), 1.8-1.6 (m, 2H), 1.33 (m, 9H).

Step c) {1-[Hydroxy-(4-methyl-thiazol-2-ylcarbamoyl)-methyl]-cyclobutyl}-carbamic acid tert-butyl ester (BB6)

The acetyl group was hydrolyzed by stirring BB6-b (56 mg, 0.15 mmol) with aqueous LiOH (1N, 0.30 mL) in 1 mL methanol for 1 h at rt. The reaction mixture was concentrated, and then partitioned between 5 ml each EtOAc and saturated aqueous NaCl. The aqueous phase was extracted further with EtOAc (2×5 mL). The organic phases were combined, dried (Na$_2$SO$_4$), and evaporated in vacuo to give 39.6 mg solids as crude material. Flash column chromatography (silica, 95/5 CH$_2$Cl$_2$-acetone) gave the title compound as white solids (36.2 mg, 71% yield). LC-UV/MS 100% DAD, AP-ES+ m/z 342 [M+H]$^+$ Building Block 7 (BB7)—a P1 Building Block

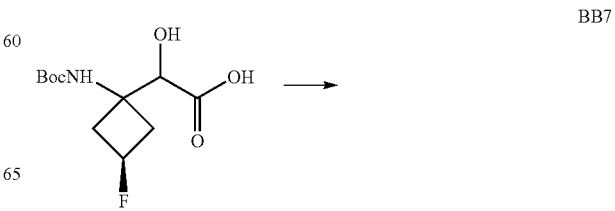

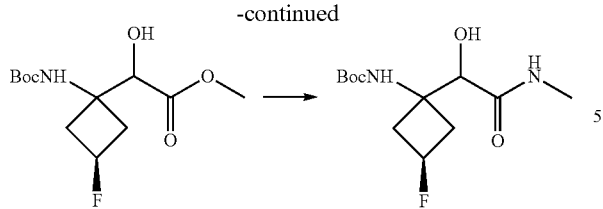

Step a) Tert-butyl 3-fluoro-1-(1-hydroxy-2-(methylamino)-2-oxoethyl)cyclobutylcarbamate (BB7)

Potassium carbonate (147.5 mg, 1.06 mmol) was added to a solution of the P1-building block BB3 (254 mg, 0.96 mmol) in DMF (5 mL) followed by addition of methyl iodide (72 µL, 1.15 mmol). The reaction mixture was stirred at room temperature for 2.5 h and then partitioned between DCM and aq. NaHCO$_3$ (sat.). The phases were separated and the organic layer was washed with water, dried (Na$_2$SO$_4$) and concentrated. The crude residue of the formed methyl ester was dissolved in a solution of methylamine in ethanol (33% (w/w), 10 mL), heated at 60° C. for 2 days and then concentrated to give the α-hydroxy amide BB7 which was pure enough to be used in the next step without further purification. MS m/z 277.4 (M+H)$^+$.

Building Block 8—a P1—Prime Side Building Block (BB8)

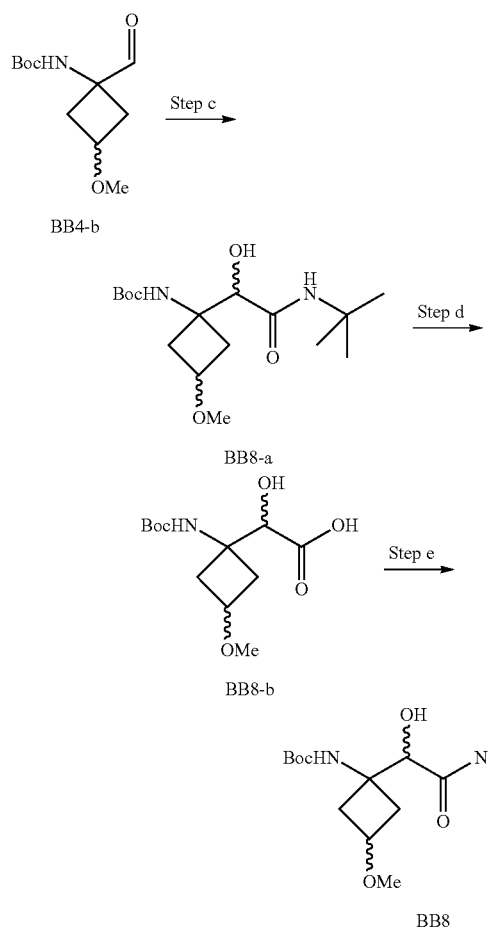

Step a) [1-(tert-Butylcarbamoyl-hydroxy-methyl)-3-methoxy-cyclobutyl]-carbamic acid tert-butyl ester (BB8-a)

Aldehyde BB4-b, 4.45 mmol, was reacted according to the procedure as described for the preparation of BB4-c, but using tert-butyl isocyanide (6.68 mmol) instead of cyclopropyl isonitrile, which gave the title compound (850 mg, 58%), (TLC: rf=0.61 (EtOAc:hexane 1:1).

Step d) (1-tert-Butoxycarbonylamino-3-methoxy-cyclobutyl)-hydroxy-acetic acid (BB8-b)

Compound DJ14 (850 mg, 2.57 mmol) was refluxed with 6N HCl (60 mL) for 16 h until the amide hydrolysis was complete. The solvent was evaporated under reduced pressure and co-evaporated with water. The product was dissolved in THF:H$_2$O (7:3 v/v, 50 mL), cooled to 0° C. and Et$_3$N (1.4 mL, 10.2 mmol) was added followed by di-tert-butyl dicarbonate (2.25 g, 10.2 mol). The mixture was stirred at room temperature overnight. The reaction mixture was washed with EtOAc followed by acidifying to pH3 with 1N HCl and extracted with EtOAc (2×50 mL). The organic layer was washed with brine and dried over anhydrous Na$_2$SO$_4$. The solvent was evaporated under reduced pressure which afforded the title P1 building block as a solid (360 mg, yield 51%).

Step e) {1-[Hydroxy-(1-methyl-1H-pyrazol-3-ylcarbamoyl)-methyl]-3-methoxy-cyclobutyl}-carbamic acid tert-butyl ester (BB8)

The hydroxy acid BB8-b was reacted with 1-methyl-1H-pyrazol-3-amine according to the procedure described in Example 1, step a, which gave the title compound (232 mg, yield 50%).

Building block 9—a P1—prime side building block (BB9)

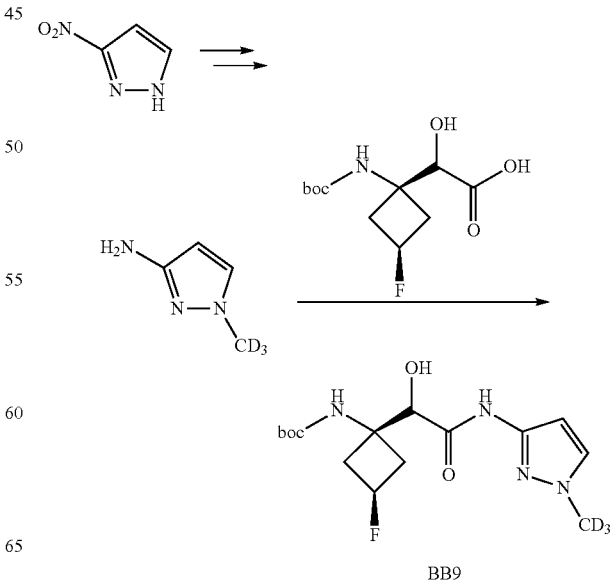

Tert-butyl (1R,3S)-3-fluoro-1-((S)-1-hydroxy-2-(1-D₃-methyl-1H-pyrazol-3-ylamino)-2-oxoethyl)cyclobutylcarbamate (BB9)

D₃-methyliodide (4.42 mmol, 0.281 mL) was added to a stirred solution of 3-nitropyrazole (4.42 mmol, 500 mg) and DBU (0.75 mL) in DMF. After 16 h, aq. NaHCO₃ was added and the mixture was extracted with DCM. The organic phase was carefully concentrated and the afforded crude product was purified by column chromatography on silica gel eluted with DCM. The afforded residue was dissolved in MeOH, hydrogenated over Pd/C-10%, filtered through Celite and concentrated, which gave 1-(D₃-methyl)-1H-pyrazol-3-ylamine. 1-(D₃-methyl)-1H-pyrazol-3-ylamine was the reacted with BB3 according to the procedure described in Example 1, step a, which gave the title compound.

Building Bloc 10—a P2-Building Block (BB10)

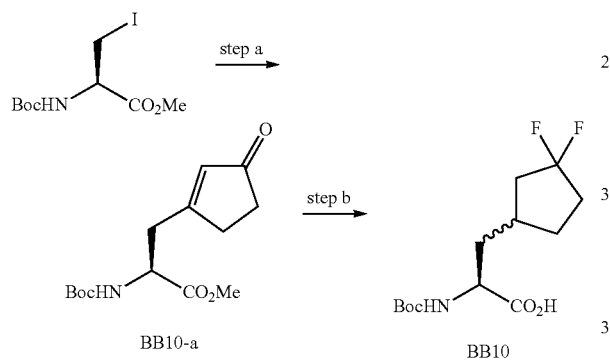

Step a) (S)-Methyl 2-(tert-butoxycarbonylamino)-3-(3-oxocyclopent-1-enyl)propanoate (BB10-a)

Boc-β-Iodo-Ala-OMe (1.0 g, 3 mmol) was added to a slurry of zinc dust (0.596 g, 9 mmol) and I₂ (0.2 mg) in 3 ml DMF under N₂. The mixture was stirred for 1 h then Pd₂ dba₃ (0.070 g, 0.076 mmol), SPhos ligand (0.062 g, 0.15 mmol), and 1,3-cyclopentanedione (0.63 g, 3.9 mmol) were added. The reaction mixture was stirred over night. Purification by flash chromatography (0-100% EtOAc in iso-hexane) gave compound the title compound (0.468 g) in 70% yield. [M+H]⁺: 284.

Step b) (S)-2-(tert-butoxycarbonylamino)-3-(3,3-difluorocyclopentyl)propanoic acid (BB10)

Compound BB10-a (0.468 g, 1.7 mmol) was dissolved in 500 ml MeOH and hydrogenated using an H-Qube with cartridge 10% Pd/C. The mixture was concentrated and used directly. 0.103 g (0.36 mmol) of the concentrated mixture was dissolved in 1.6 ml DCM and cooled on ice (0° C.). Deoxofluor (313 μl 50% in THF, 0.72 mmol) and of EtOH (10 drops) were added. The reaction mixture was allowed to attain room temperature over three days, and then purified by flash chromatography (0-100% EtOAc in iso-hexane). The afforded di-fluorinated compound was hydrolysed by LiOH (0.009 g, 0.037 mmol) in THF/MeOH (5:3; 3.5 ml) for 4 h at room temperature whereafter the reaction mixture was acidified with 5% citric acid (aq), extracted with DCM and dried (Na₂SO₄). After concentration the title compound was achieved in 33% yield as a diastereomeric mixture. 292.

Building Block 11—a P1-Prime Side Building Block (BB11)

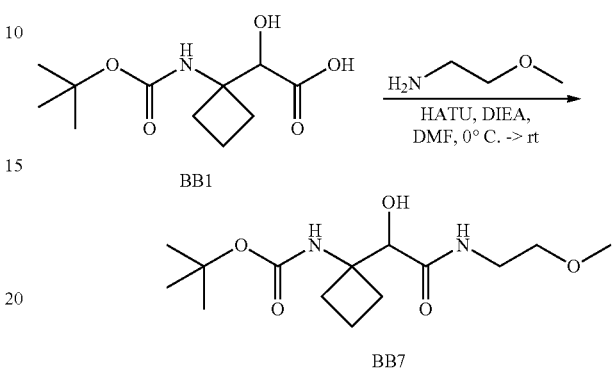

Tert-butyl 1-(1-hydroxy-2-(2-methoxyethylamino)-2-oxoethyl)cyclobutylcarbamate (BB7)

To a round-bottomed flask with BB1 (200 mg, 0.815 mmol) dissolved in DMF (10 mL) was added 2-methoxyethanamine (78 μL, 0.897 mmol) and DIEA (540 mL, 3.26 mmol). The flask was placed in an ice bath and after 10 minutes HATU (310 mg, 0.815 mmol) was added. After 1 hr the solvent was removed by rotary evaporation and the crude dissolved in 50 mL ethyl acetate. The organic phase was washed with 20 mL of 1 M HCl followed by 20 mL of sat. NaHCO₃. The organic phase was dried (Na₂SO₄), filtered and evaporated on silica. The crude on silica was purified by flash chromatography using pure ethyl acetate as mobile phase and the product was obtained in quantitative yield (245 mg), 303.2 [M+H]⁺.

Example 1

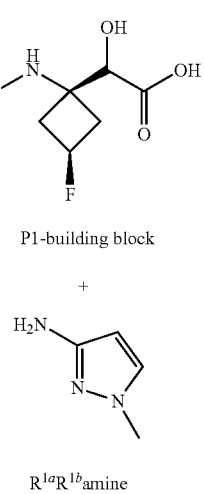

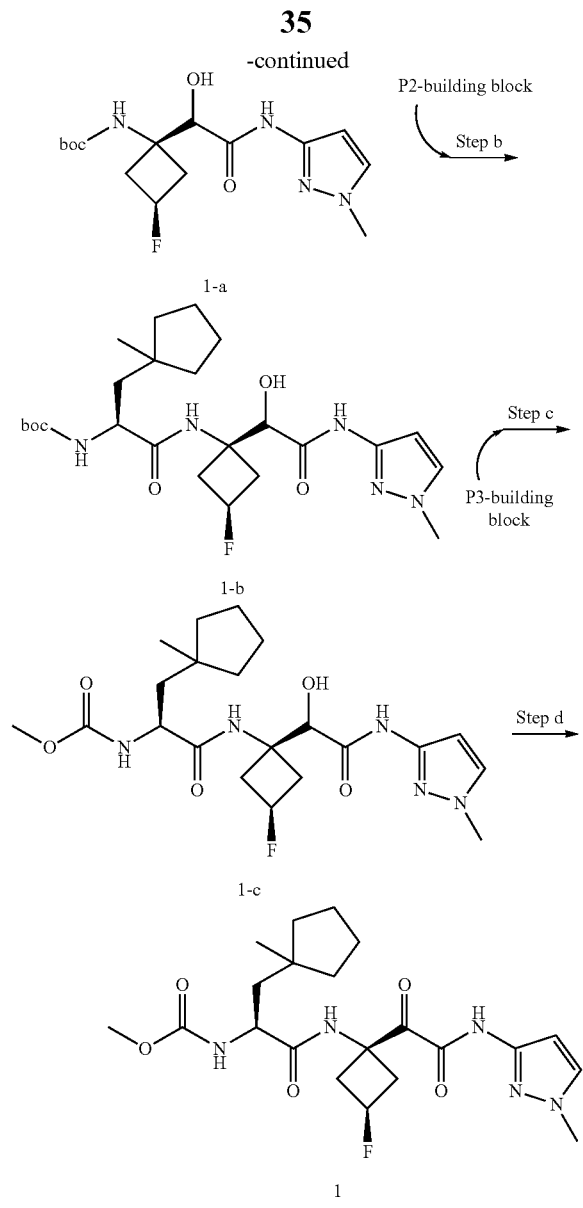

Step a) {3-Fluoro-1-[hydroxy-(1-methyl-1H-pyrazol-3-ylcarbamoyl)-methyl]-cyclobutyl}-carbamic acid tert-butyl ester (1-a)

1-Methyl-1H-pyrazol-3-amine (1 eq.) and DIEA (4 eq) was added to a solution of the P1-building block BB3 (1 eq) dissolved in DMF. The solution was cooled to 0° C. and after 10 minutes HATU (1 eq) was added. After approximately 2 hours at RT, LC-MS showed product and no starting material and the solvent was removed by rotary evaporation. The crude product was dissolved in 40 mL EtOAc and washed with 25 mL sat. NaHCO$_{3(aq)}$. The organic phase was dried with Na$_2$SO$_4$, filtered and evaporated to dryness. The crude product was purified on a 25 g silica column on a Biotage Flashmaster, which gave the title compound.

Step b) 2-(1-Amino-3-fluoro-cyclobutyl)-2-hydroxy-N-(1-methyl-1H-pyrazol-3-yl)-acetamide (1-b)

Compound 1-a (363 mg, 1.06 mmol) was treated with a 7.5 mL of a mixture of TFA:DCM:TIS:water (20:80:1:1). After 2 h at room temperature, LC/MS analysis confirmed complete removal of the Boc group and the solution was concentrated in vacuo and azeotroped with dichloromethane (3×) to remove excess TFA. The crude product (339 mg, 0.9 mmol) was dissolved in DCM (10 mL) and added to a solution of 2-amino-3-(1-methyl-cyclopentyl)-propionamide (prepared as described in Ex. 1 of WO2006/064286) (1.2 eq), PyBOP (1.2 eq) and diisopropylethylamine (4 eq) in DCM (5 mL) that had been stirred at room temperature for 5 min The mixture was stirred at room temperature until LC/MS analysis indicated complete amide formation (~30 min) DCM was added to the reaction and the organic phase was washed with 0.1 M HCl (aq) (2×) and 10% NaHCO$_3$ (aq) (2×). The organic phase was dried and concentrated in vacuo to afford the title compound which was used in subsequent step without further purification.

Step c) N-{3-Fluoro-1-[hydroxy-(1-methyl-1H-pyrazol-3-ylcarbamoyl)-methyl]-cyclobutyl}-3-(1-methyl-cyclopentyl)-2-propionylamino-propionamide (1-c)

Compound 1-b (0.9 mmol) was treated with a 7.5 mL of a mixture of TFA:DCM:TIS:water (20:80:1:1). After 2 h at room temperature, LC/MS analysis confirmed complete removal of the BOC group and the solution was concentrated in vacuo and azeotroped with dichloromethane (3×) to remove excess TFA. The residue was dissolved in DCM and extracted with 0.1M HCl (aq) (3×). The pooled aqueous layers were basified to pH 10 with NaOH (aq) and the product extracted with DCM (3×). The pooled organic layers were dried (MgSO$_4$) and concentrated in vacuo. The afforded crude compound (33 mg, 83 mmol) was dissolved in DCM (2 mL) and DIEA (3 eq.) and methyl chloroformate (91.3 mmol) was added. The reaction was stirred at room temperature for 1 h after which time LC/MS analysis indicated complete acylation. The reaction was quenched by addition of Methanol (0.5 mL) and the reaction was concentrated in vacuo. The residue was dissolved in DCM (5 mL) and the organic phase was washed with 0.1M HCl (aq) (2×) and 10% NaHOC$_3$ (aq) (2×), eluted through a hydrophobic Phase separator and concentrated in vacuo, which gave the title compound.

Step d) N-[3-Fluoro-1-(1-methyl-1H-pyrazol-3-ylaminooxalyl)-cyclobutyl]-3-(1-methyl-cyclopentyl)-2-propionylamino-propionamide (1)

The residue afforded in step c was re-dissolved in DCM (1.5 mL) and Dess-Martin periodinane (91.3 mmol) was added in one portion at room temperature. The reaction was stirred at room temperature for 2 h after which time LC/MS analysis indicated complete oxidation. The reaction mixture was diluted with DCM and the solution washed with a 1:1 mixture of 10% Na$_2$S$_2$O$_3$ (aq) and 10% NaHCO$_3$ (aq). The organic layer was eluted through a hydrophobic Phase Separator and concentrated in vacuo. The residue was purified by preparative LC/MS to afford the target compound in 31% overall yield, M/Z 452.2 [M+H]$^+$ Examples 2-8

The compounds illustrated in the table below were prepared analogously to the procedure outlined in Example 1 using the appropriate $R^{1a}R^{1b}$ amines, P1/P2 and P3 building blocks, followed by Dess Martin oxidation to the end product α-keto amide.

TABLE 1

TABLE 1

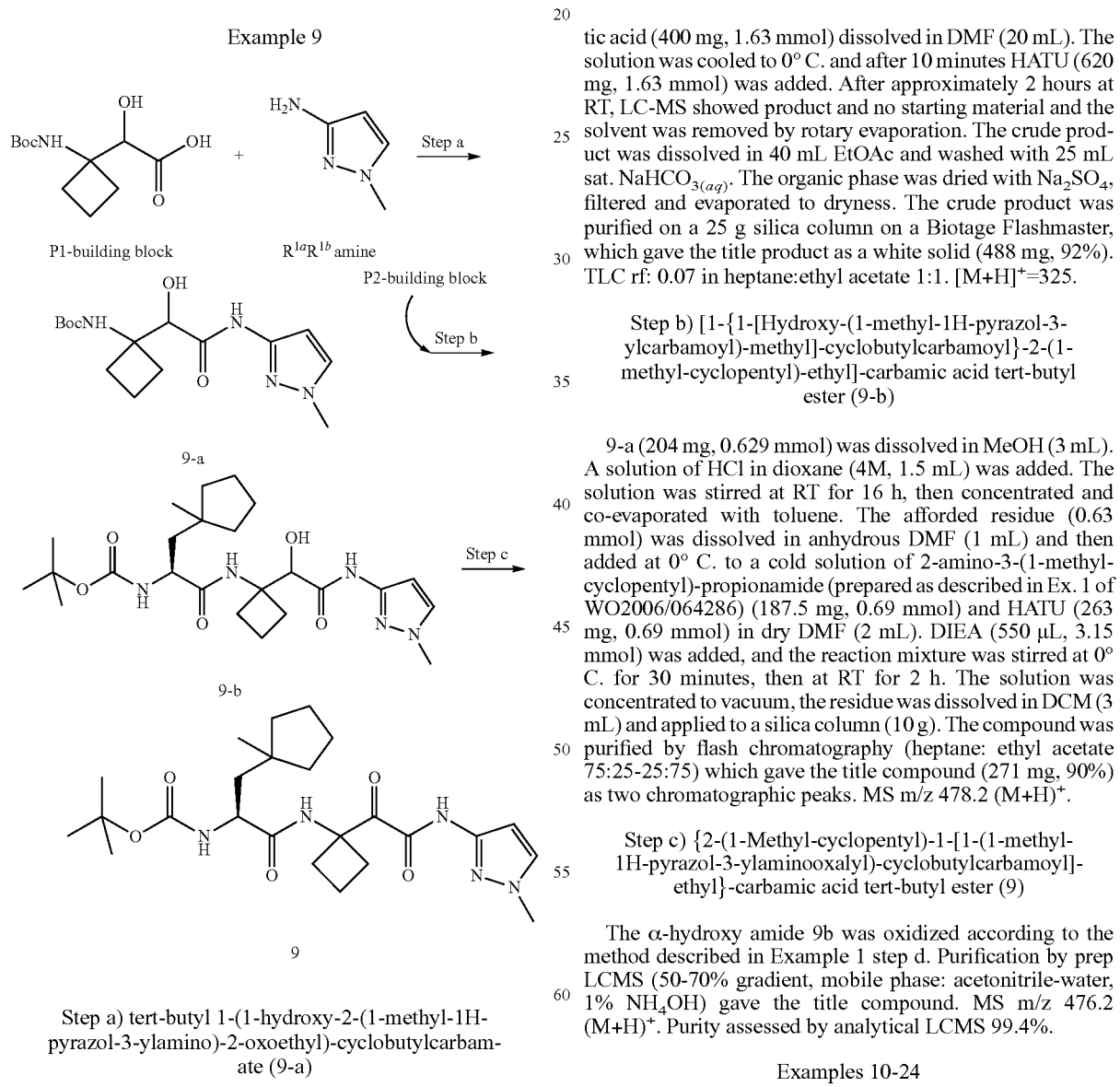

| Ex. | R⁴' | R³ | R²ᵃ | R²ᵇ | R¹ᵇ | [M + H]⁺ |
|---|---|---|---|---|---|---|
| 2 | isobutyl | 1-methylcyclopentyl-methyl | F | H | 1-methylpyrazol-3-yl | 494.3 |
| 3 | isopropyl | 1-methylcyclopentyl-methyl | F | H | 1-methylpyrazol-3-yl | 490.25 |
| 4 | ethyl | homo-t-butyl | F | H | 1-methylpyrazol-3-yl | 440.12 |
| 5 | isobutyl | homo-t-butyl | F | H | 1-methylpyrazol-3-yl | 468.18 |
| 6[1] | ethyl | 1-fluorocyclopentyl-methyl | F | H | 1-methylpyrazol-3-yl | 469.9 |
| 7[1] | isobutyl | 1-fluorocyclopentyl-methyl | F | H | 1-methylpyrazol-3-yl | 497.9 |
| 8 | ethyl | 1-methylcyclopentyl-methyl | F | H | 1-methylpyrazol-3-yl | 466.3 |

[1]Removal of the Boc group was performed using 4M HCl in dioxane

Example 9

Step a) tert-butyl 1-(1-hydroxy-2-(1-methyl-1H-pyrazol-3-ylamino)-2-oxoethyl)-cyclobutylcarbamate (9-a)

1-Methyl-1H-pyrazol-3-amine (158 mg, 1.63 mmol) and DIEA (1.08 mL, 6.52 mmol) was added to a solution of 2-(1-(tert-butoxycarbonylamino)cyclobutyl)-2-hydroxyacetic acid (400 mg, 1.63 mmol) dissolved in DMF (20 mL). The solution was cooled to 0° C. and after 10 minutes HATU (620 mg, 1.63 mmol) was added. After approximately 2 hours at RT, LC-MS showed product and no starting material and the solvent was removed by rotary evaporation. The crude product was dissolved in 40 mL EtOAc and washed with 25 mL sat. NaHCO$_{3(aq)}$. The organic phase was dried with Na$_2$SO$_4$, filtered and evaporated to dryness. The crude product was purified on a 25 g silica column on a Biotage Flashmaster, which gave the title product as a white solid (488 mg, 92%). TLC rf: 0.07 in heptane:ethyl acetate 1:1. [M+H]⁺=325.

Step b) [1-{1-[Hydroxy-(1-methyl-1H-pyrazol-3-ylcarbamoyl)-methyl]-cyclobutylcarbamoyl}-2-(1-methyl-cyclopentyl)-ethyl]-carbamic acid tert-butyl ester (9-b)

9-a (204 mg, 0.629 mmol) was dissolved in MeOH (3 mL). A solution of HCl in dioxane (4M, 1.5 mL) was added. The solution was stirred at RT for 16 h, then concentrated and co-evaporated with toluene. The afforded residue (0.63 mmol) was dissolved in anhydrous DMF (1 mL) and then added at 0° C. to a cold solution of 2-amino-3-(1-methyl-cyclopentyl)-propionamide (prepared as described in Ex. 1 of WO2006/064286) (187.5 mg, 0.69 mmol) and HATU (263 mg, 0.69 mmol) in dry DMF (2 mL). DIEA (550 µL, 3.15 mmol) was added, and the reaction mixture was stirred at 0° C. for 30 minutes, then at RT for 2 h. The solution was concentrated to vacuum, the residue was dissolved in DCM (3 mL) and applied to a silica column (10 g). The compound was purified by flash chromatography (heptane: ethyl acetate 75:25-25:75) which gave the title compound (271 mg, 90%) as two chromatographic peaks. MS m/z 478.2 (M+H)⁺.

Step c) {2-(1-Methyl-cyclopentyl)-1-[1-(1-methyl-1H-pyrazol-3-ylaminooxalyl)-cyclobutylcarbamoyl]-ethyl}-carbamic acid tert-butyl ester (9)

The α-hydroxy amide 9b was oxidized according to the method described in Example 1 step d. Purification by prep LCMS (50-70% gradient, mobile phase: acetonitrile-water, 1% NH$_4$OH) gave the title compound. MS m/z 476.2 (M+H)⁺. Purity assessed by analytical LCMS 99.4%.

Examples 10-24

The compounds illustrated in the table below were prepared analogously to the procedure outlined in Example 9, using the appropriate building blocks and P1' amines.

TABLE 2

| Ex. | R³ | R²ᵃ | R²ᵇ | R¹ᵇ | [M + H]⁺ |
|---|---|---|---|---|---|
| 10[1,2] | 1-fluorocyclopentylmethyl | F | F | 1-methylpyrazol-3-yl | 516.1 |
| 11[1,3] | 1-methylcyclopentylmethyl | H | H | 1-methyl-1H-imidazol-4-yl | 476.2 |
| 12[5] | 1-methylcyclopentylmethyl | F | F | 1-methylpyrazol-3-yl | 512 |
| 13[5] | 2-fluoro-2-methylbutyl | F | F | 1-methylpyrazol-3-yl | 490 |
| 14[5] | 1-methylcyclobutylmethyl | F | F | 1-methylpyrazol-3-yl | 498 |
| 15[5] | cyclohexylmethyl | F | F | 1-methylpyrazol-3-yl | 512 |
| 16[5] | homo-t-butyl | F | F | 1-methylpyrazol-3-yl | 486 |
| 17[4,5] | 1-methylcyclopentylmethyl | OMe | H | cyclopropyl | 466 |
| 18[5] | 1-fluorocyclopentylmethyl | F | H | 1-methylpyrazol-3-yl | 498 |
| 19[5] | 1-methylcyclobutylmethyl | F | H | 1-methylpyrazol-3-yl | 480 |
| 20 | 1-methylcyclopentylmethyl | H | H | 4-methylthiazol-2-yl | 493 |
| 21 | 1-methylcyclopentylmethyl | F | H | cyclopropyl | 440 |
| 22 | 1-fluorocyclopentylmethyl | F | H | cyclopropyl | na |
| 23 | 1-fluorocyclopentylmethyl | F | H | cyclopropyl | na |
| 24 | 1-methylcyclopentylmethyl | H | H | cyclopropyl | na |

[1]Removal of the Boc in step b was performed using TFA-H₂O-TIS.
[2]In step b, the P2 building block was coupled to the P1-P1' building block using DMF as solvent and PyBOP as coupling agent.
[3]The P1'-amine was prepared by reduction of the corresponding nitro compound and coupled to the P1 building block using HATU as coupling agent.
[4]The stereochemistry at the steric centre to which R²ᵃ and R²ᵇ is attached, is not defined.
[5]Removal of the Boc group in step b was performed using MeOH:AcCl 9:1.

Example 25

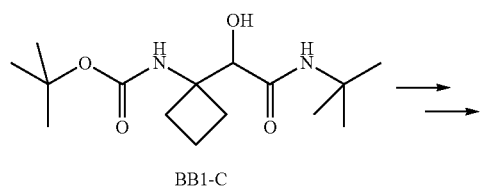

(S)-tert-butyl 1-(1-(2-(tert-butylamino)-2-oxoacetyl)cyclobutylamino)-3-(1-methylcyclopentyl)propan-2-ylcarbamate (25)

BB1-c (85 mg, 0.283 mmol) was coupled to (S)-2-(tert-butoxycarbonylamino)-3-(1-methylcyclopentyl)propanoic acid according to the method described in Example 9 step b. The crude product was purified with flash chromatography using heptane:EtOAc 2:1. which gave the α-hydroxy amide (103 mg, 80%). [M+H]⁺=454.

The afforded α-hydroxy amide (10 mg, 0.0221 mmol) was oxidized according to the method described Example 1, step d, which after purification by flash chromatography using heptane: EtOAc (2:1 to 1:1) and lyophilisation of appropriate fractions, gave the title compound (11.4 mg, 55%). [M+H]⁺= 452.

Examples 26-43

The compounds illustrated in the table below were prepared analogously to the procedure outlined in Example 1 using the appropriate R¹ᵃR¹ᵇ amines, P1/P2 building blocks and chloroformate, followed by Dess Martin oxidation to the end product α-keto amide.

TABLE 3

| Ex. | R⁴' | R³ | R²ᵃ | R²ᵇ | R¹ᵇ | [M + H]⁺ |
|---|---|---|---|---|---|---|
| 26 | ethyl | 1-fluorocyclopentylmethyl | F | H | cyclopropyl | 430.2 |
| 27 | ethyl | 1-methylcyclobutylmethyl | F | H | 1-methylpyrazol-3-yl | 452.3 |

TABLE 3-continued

| Ex. | $R^{4'}$ | $R^3$ | $R^{2a}$ | $R^{2b}$ | $R^{1b}$ | $[M + H]^+$ |
|---|---|---|---|---|---|---|
| 28 | ethyl | 1-fluorocyclopentylmethyl | F | H | methyl | 402.4[2] |
| 29[1] | D₃-methyl | 1-fluorocyclopentylmethyl | F | H | 1-methylpyrazol-3-yl | 459.0 |
| 30[1] | methyl | 1-fluorocyclopentylmethyl | F | H | 1-methylpyrazol-3-yl | 456.3 |
| 31[1] | isopropyl | 1-fluorocyclopentylmethyl | F | H | 1-methylpyrazol-3-yl | 484.0 |
| 32[1] | n-propyl | 1-fluorocyclopentylmethyl | F | H | 1-methylpyrazol-3-yl | 484.0 |
| 33[1] | s-butyl | 1-fluorocyclopentylmethyl | F | H | 1-methylpyrazol-3-yl | 498.4 |
| 34 | ethyl | 4,4'-difluorocyclohexyl-methyl | F | H | 1-methylpyrazol-3-yl | 502.3 |
| 35[3] | ethyl | 1-fluorocyclopentylmethyl | OMe | H | 1-methylpyrazol-3-yl | 482.3 |
| 36 | isopropyl | 1-fluorocyclopentylmethyl | H | H | 1-methylpyrazol-3-yl | 466.2 |
| 37 | methyl | 1-fluorocyclopentylmethyl | H | H | 1-methylpyrazol-3-yl | 438.1 |
| 38[4] | methyl | 1-fluorocyclopentylmethyl | H | H | 1-methyl-4-chloro-pyrazol-3-yl[4] | 471.8 |
| 39 | ethyl | 1-fluorocyclopentylmethyl | F | H | 1-(D₃-methyl)-pyrazol-3-yl | 473.1 |
| 40 | ethyl | 1-fluorocyclopentylmethyl | F | F | 1-methylpyrazol-3-yl | 488.2 |
| 41[2] | ethyl | 1-fluorocyclopentylmethyl | H | H | 1-methylpyrazol-3-yl | 402.4 |
| 42[1] | methyl | 1-fluorocyclopentylmethyl | F | F | 1-methylpyrazol-3-yl | 474.34 |
| 43 | ethyl | 1-methycyclopentylmethyl | H | H | 2-methoxyethyl | 426 |

[1]Removal of the Boc group was performed using 4M HCl in dioxane.
[2]MS was measured in negative mode, i.e. peak is $[M - H]^-$.
[3]The isomeric ratio of the OMe in $R^{2a}/R^{2b}$ is 1:1.
[4]The oxidation in step b was performed on the crude α-hydroxy amide afforded in step a.

Examples 44-56

The compounds illustrated in the table below were prepared analogously to the procedure outlined in Example 9, using the appropriate building blocks and P1' amines.

TABLE 4

| Ex. | $R^3$ | $R^{2a}$ | $R^{2b}$ | $R^{1b}$ | $[M + H]^+$ |
|---|---|---|---|---|---|
| 44[4] | 1-fluorocyclopentylmethyl | H | H | 2-methoxyethyl | 458 |
| 45 | cyclopentylmethyl | F | H | 1-methylpyrazol-3-yl | 478.3 |
| 46 | cyclobutylmethyl | F | H | 1-methylpyrazol-3-yl | 464.4 |
| 47 | 1-fluorocyclopentylmethyl | F | H | methyl | 430.4 |
| 48 | 4,4'-difluorocyclohexylmethyl | F | H | 1-methylpyrazol-3-yl | 530.3 |
| 49[2] | 1-fluorocyclopentylmethyl | OMe | H | 1-methylpyrazol-3-yl | 510.4 |
| 50 | 1-fluorocyclopentylmethyl | F | H | 1-(D₃-methyl)-pyrazol-3-yl | 501.2 |
| 51 | 1-fluorocyclopentylmethyl | F | H | 1-methylpyrazol-4-yl | 498.1 |
| 52 | 1-fluorocyclopentylmethyl | H | H | 1-methylpyrazol-3-yl | 480.1 |
| 53[2] | cyclohexylethyl | H | H | 1-methylpyrazol-3-yl | 490.40 |
| 54[1,3] | homo-t.butyl | H | H | 3-isoxazole | 435.28 |
| 55[4] | 1-methylcyclopentylmethyl | H | H | 2-methoxyethyl | 454 |

[1]MS was measured in negative mode, i.e. peak is $[M - H]^-$.
[2]The stereochemistry at the steric centre to which $R^{2a}$ and $R^{2b}$ are attached, is not defined.
[3]In step a the 3-aminoisoxazole was coupled to the P1 using EtCO₂Cl as coupling agent. MeOH/sat. K₂CO₃ (aq.), 1:1 was used during work-up.
[4]In step b, removal of the Boc group was performed using MeOH:AcCl 9:1.

Example 56

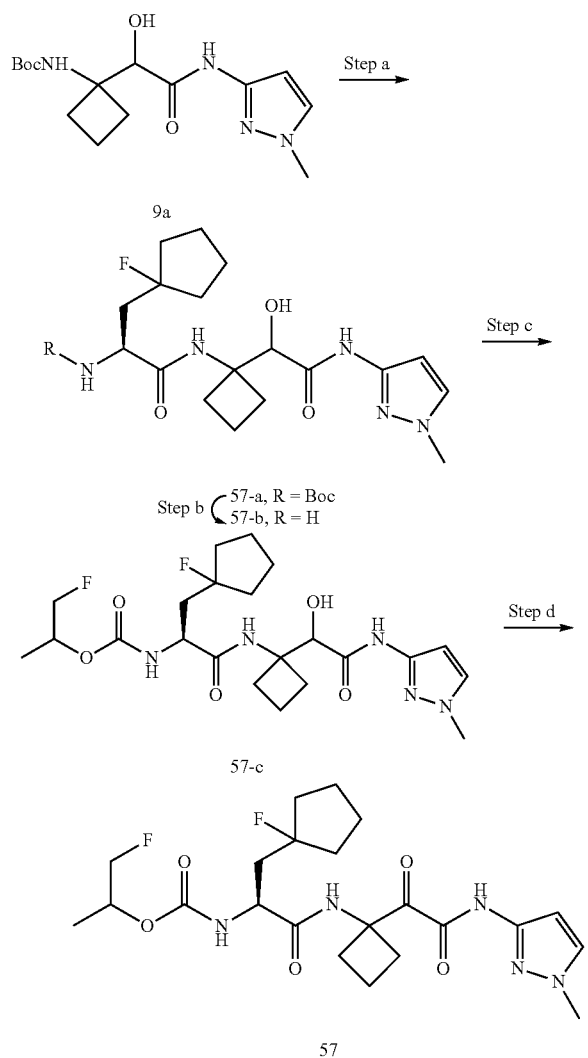

Step a) (2-(1-Fluoro-cyclopentyl)-1-{1-[hydroxy-(1-methyl-1H-pyrazol-3-ylcarbamoyl)-methyl]-cyclobutylcarbamoyl}-ethyl)-carbamic acid tert-butyl ester (56-a)

Carbamate 9a was treated with 4M HCl in 1,4-dioxane to remove the Boc protecting group. The afforded bis-HCl salt (220 mg, 0.74 mmol) was dissolved in DMF (2 mL) and DIPEA (260 μL, 1.5 mmol) was added and the mixture was cooled to 0° C. In a separate flask (2R,3R)-2-(tert-butoxycarbonylamino)-3-cyclopentyl-3-fluoropropanoic acid (201 mg, 0.74 mmol, prepared as described in WO06/064286) was dissolved in DMF and DIPEA (385 μL, 2.2 mmol) was added and the mixture was cooled to 0° C. whereafter HATU (295 mg, 0.77 mmol) was added and the reaction was stirred for 5 min. The contents of the second flask were added dropwise to the first flask and the stirring was continued for 1 h. Sat aq NaHCO₃ (15 mL) and Et₂O (15 mL) were added and the phases were separated. The aqueous phase was extracted with 2×15 mL EtOAc and the combined organic layers were washed with sat aq NaHCO₃ (15 mL). The solvent was removed by rotary evaporation and the product was purified by gradient column chromatography (DCM-6% MeOH in DCM). This gave the title compound (332 mg, 93%). ES+ 482.2 [M+H]⁺.

Step b) 2-Amino-3-(1-fluoro-cyclopentyl)-N-{1-[hydroxy-(1-methyl-1H-pyrazol-3-ylcarbamoyl)-methyl]-cyclobutyl}-propionamide (56-b)

The Boc-protected amine 56-a (332 mg, 0.689 mmol) was added 4M HCl in 1,4-dioxane (5 mL) and the reaction was stirred for 20 min. The product was isolated by degassing the reaction (N₂/vacuum cycles) followed by lyophilisation. This gave the title compound as the bis HCl salt (310 mg, >99%). ES+ 382.1 [M+H]⁺.

Step c) (2-(1-Fluoro-cyclopentyl)-1-{1-[hydroxy-(1-methyl-1H-pyrazol-3-ylcarbamoyl)-methyl]-cyclobutylcarbamoyl}-ethyl)-carbamic acid 2-fluoro-1-methyl-ethyl ester (56-c)

1-fluoropropane-2-ol (38 mg, 0.48 mmol) and pyridine (39 μL, 0.48 mmol) were dissolved in DCM (1.5 mL), and the mixture was stirred and cooled to 0° C. Phosgene (1.9 M solution in toluene, 232 μL, 0.44 mmol) was added in one portion and the reaction was allowed to warm to rt and was stirred for 3 h during which a white precipitate formed. In a separate flask, the amine 56-b (36 mg, 0.080 mmol) and DIPEA (45 μL, 0.26 mmol) were dissolved in DCM (1 mL) and the mixture was stirred and cooled to 0° C. 250 μL of the mixture in the first flask were added to the second, and the reaction was monitored by HPLC. Another 250 μL aliquot was added after 15 min and the reaction was stirred for 15 more minutes after which it was quenched by the addition of sat aq NaHCO₃ (10 mL) and Et₂O (10 mL). The layers were separated and the aqueous phase was extracted with 2×5 mL EtOAc. The combined organic phases were washed with sat aq NaHCO₃ (5 mL) and the solvent was removed by rotary evaporation. The product was purified by gradient column chromatography (DCM-10% MeOH in DCM). This gave the title compound as a mixture of diastereomers (22 mg, 57%). ES+ 486.3 [M+H]⁺.

Step d) {2-(1-Fluoro-cyclopentyl)-1-[1-(1-methyl-1H-pyrazol-3-ylaminooxalyl)-cyclobutylcarbamoyl]-ethyl}-carbamic acid 2-fluoro-1-methyl-ethyl ester (56)

The α-hydroxy amide 58-c was oxidized and the product was purified as described in Example 1 step d, which gave the title compound as a mixture of diastereomers (16 mg, 74%). Purity 99.7% (LC/MS-DAD), ES+ 483.3.

Example 57

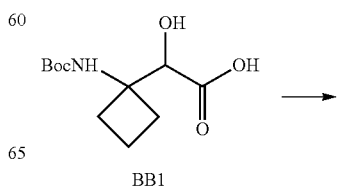

BB1

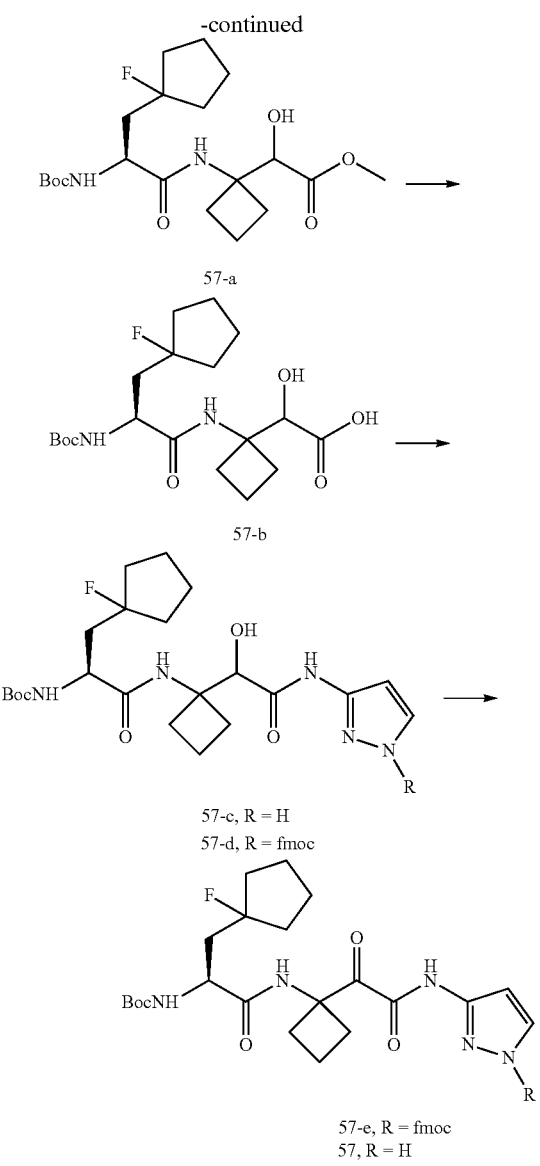

57-a 57-b 57-c, R = H
57-d, R = fmoc 57-e, R = fmoc
57, R = H

Step a) {2-(1-Fluoro-cyclopentyl)-1-[1-(1H-pyrazol-3-ylaminooxalyl)-cyclobutylcarbamoyl]-ethyl}-carbamic acid tert-butyl ester (57-a)

BB1 (350 mg, 1.43 mmol) was dissolved in MeOH (4 mL) and treated with HCl (4M in dioxane, 2 mL). After 3.5 h the solution was concentrated and the residue co-evaporated with toluene. The resulting amine was added to a solution of 2-tert-butoxycarbonylamino-3-(1-fluorocyclopentyl)-propionic acid (393 mg, 1.43 mmol), HATU (543 mg, 1.43 mmol) and DIEA (1 ml, 1.43 mmol) in anh. DMF at 0° C. The reaction mixture was allowed to reach room temperature and was stirred for 16 h. The solution was concentrated and the afforded residue was purified by flash chromatography on silica gel column (EtOAc/iso-hexane, 20:80-40:60) which gave the title compound (767 mg) MS m/z 417.2 (M+H)$^+$.

Step b) {1-[2-tert-Butoxycarbonylamino-3-(1-fluoro-cyclopentyl)-propionylamino]-cyclobutyl}-hydroxy-acetic acid (57-b)

LiOH (0.5M aqueous solution, 0.64 mmol, 1.264 mL) was added to a solution of compound 57-a (131.9 mg, 0.32 mmol) in acetonitrile: THF 1:1 (2.4 mL). The reaction mixture was stirred at room temperature for 40 min then acidified with 1M HCl (1.5 mL). Water and ethyl acetate were added to the solution and the organic phase was separated, washed with acidic water, dried (Na$_2$SO$_4$) and concentrated which gave the title compound (150 mg). MS m/z 403.2 (M+H)$^+$.

Step c) (2-(1-Fluoro-cyclopentyl)-1-{1-[hydroxy-(1H-pyrazol-3-ylcarbamoyl)-methyl]-cyclobutylcarbamoyl}-ethyl)-carbamic acid tert-butyl ester (57-c)

3-Aminopyrazole (92 mg, 1.08 mmol) and DIEA (110 µL, 1.08 mmol) were added to a solution of compound 57-b (0.31 mmol) in anh. DMF (3 mL). The solution was cooled to 0° C. and stirred for 2-3 minutes, then HATU (126 mg, 0.32 mmol) in anh. DMF (1 mL) was added. The reaction mixture was allowed to attain room temperature, stirred for 16 h and then diluted with DCM. The organic phase was extracted with NaHCO$_3$ sat. aq. solution. The aqueous phase was extracted with ethyl acetate and the combined organics dried over anh. Na$_2$SO$_4$ and then concentrated. Purification by flash column chromatography (MeOH/DCM, 0:1-2:8) gave the title compound (91 mg g, 63%). MS m/z 468.3 (M+H)$^+$.

Step d) 3-(2-{1-[2-tert-Butoxycarbonylamino-3-(1-fluoro-cyclopentyl)-propionylamino]-cyclobutyl}-2-hydroxy-acetylamino)-pyrazole-1-carboxylic acid 9H-fluoren-9-ylmethyl ester (57-d)

Compound 57-c (22.5 mg, 0.0482 mmol) was dissolved in a mixture of dioxane:water 1:1 (4 mL). NaHCO$_3$ (14.2 mg, 0.168 mmol) was added to the solution followed by addition of Fmoc-Cl (48 mg, 0.18 mmol). The reaction mixture was stirred at room temperature for 16 h, diluted with DCM and extracted. The organic phase was washed with brine, dried over anh. Na$_2$SO$_4$ and concentrated. Purification by flash column chromatography (EtOAc/iso-Hexane, 0:100-40:60) gave the title compound (28 mg, 84%). MS m/z 690.3 (M+H)$^+$.

Step e) 3-(2-{1-[2-tert-Butoxycarbonylamino-3-(1-fluoro-cyclopentyl)-propionylamino]-cyclobutyl}-2-oxo-acetylamino)-pyrazole-1-carboxylic acid 9H-fluoren-9-ylmethyl ester (57-e)

Dess-Martin periodinane (24 mg, 0.056 mmol) was added to a solution of alcohol 57-d (28 mg, 0.04 mmol) in anh. DCE (3 ml). The reaction mixture was stirred at room temperature for 40 min and then quenched with 10% aq. Na$_2$S$_2$O$_3$ and aq. NaHCO$_3$ (sat.). The phases were separated and the organic layer was dried (Na$_2$SO$_4$) and concentrated. Purification by flash column chromatography (EtOAc/iso-Hexane, 0:100-40:60) gave the title compound (21.7 mg, 79%). MS m/z 688.18 (M+H)$^+$.

Step f) {2-(1-Fluoro-cyclopentyl)-1-[1-(1H-pyrazol-3-ylaminooxalyl)-cyclobutylcarbamoyl]-ethyl}-carbamic acid tert-butyl ester (57)

To a solution of compound 57-e (0.015 mmol) in acetonitrile:THF:water 1:1:0.5 (1.25 mL) was added LiOH (0.5M aqueous solution, 0.015 mmol, 31.5 µL). The reaction mixture was stirred at room temperature for 5 min and then acidified with 1M HCl (30 µL). Water and ethyl acetate were added, and the organic phase was separated, washed with acidic water, dried (Na$_2$SO$_4$) and concentrated. The afforded residue was purified by flash column chromatography

Example 58

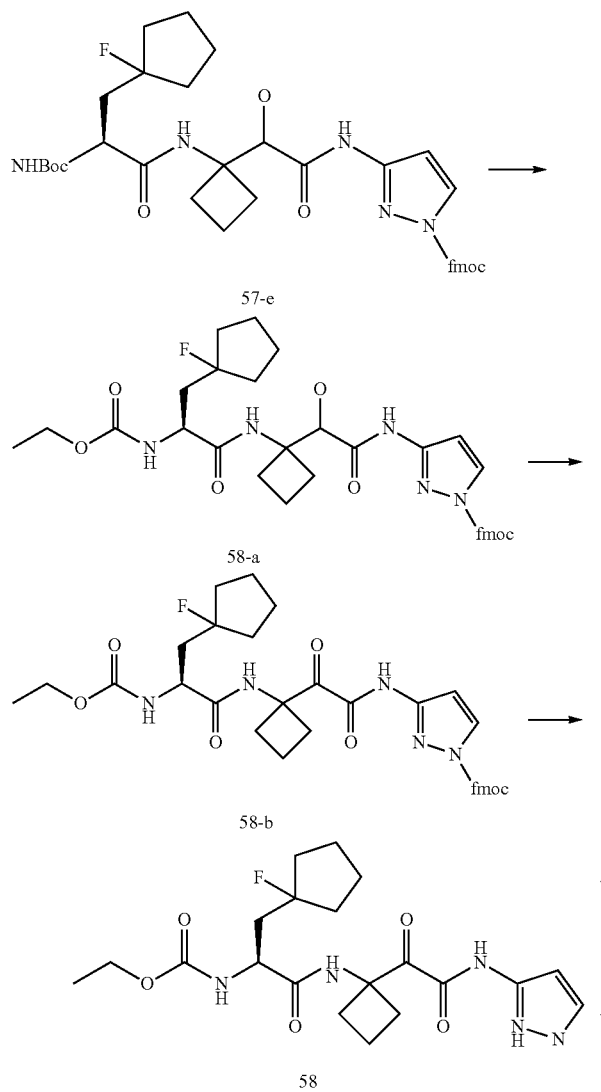

Step a) 3-(2-{1-[2-Ethoxycarbonylamino-3-(1-fluoro-cyclopentyl)-propionylamino]-cyclobutyl}-2-hydroxy-acetylamino)-pyrazole-1-carboxylic acid 9H-fluoren-9-ylmethyl ester (58-a)

Compound 57-e (0.079 mmol) was dissolved in 4M HCl in dioxane (3 mL) and then stirred for 4 hrs at room temperature. The solution was concentrated under vacuum and the crude portioned between aq. $K_2CO_3$ (0.5 M) and DCM. The aqueous phase was extracted with EtOAc, the combined organic layers were dried over anh. $Na_2SO_4$ and concentrated under vacuum. The resulting amine was dissolved in dry DCM (3 mL) and an excess of solid $NaHCO_3$ was added, followed by addition of ethyl chloroformate (7.5 µL, 0.079 mmol). The reaction was stirred for 2 hrs, then filtered and concentrated. (MS m/z 662.05 (M+H).+ The crude compound was used in next step without further purification.

Step b) 3-(2-{1-[2-Ethoxycarbonylamino-3-(1-fluoro-cyclopentyl)-propionylamino]-cyclobutyl}-2-oxo-acetylamino)-pyrazole-1-carboxylic acid 9H-fluoren-9-ylmethyl ester (58-b)

Dess-Martin periodinane (47 mg, 0.11 mmol) was added to a solution of alcohol 58-a (0.079 mmol) in anh. DCE (3 ml). The reaction mixture was stirred at room temperature for 90 min and then quenched with 10% aq. $Na_2S_2O_3$ and aq. $NaHCO_3$ (sat.). The phases were separated and the organic layer was dried ($Na_2SO_4$) and concentrated. Purification by flash column chromatography (EtOAc/iso-Hexane, 0:100-40:60) gave the title compound (6.5 mg, 13%). MS m/z 660.1 (M+H)+.

Step c) {2-(1-Fluoro-cyclopentyl)-1-[1-(2H-pyrazol-3-ylaminooxalyl)-cyclobutylcarbamoyl]-ethyl}-carbamic acid ethyl ester (58)

Compound 58-b (0.01 mmol) was reacted according to the procedure described in Example 57 step f, which gave the title compound (1 mg, 23%). MS m/z 437.95 (M+H)+.

Example 59

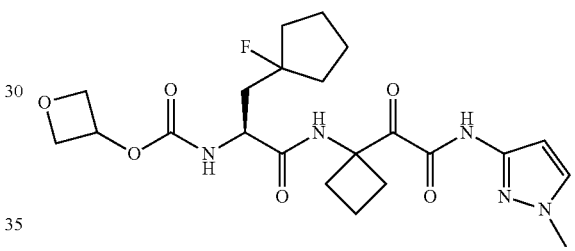

{2-(1-Fluoro-cyclopentyl)-1-[1-(1-methyl-1H-pyrazol-3-ylaminooxalyl)-cyclobutylcarbamoyl]-ethyl}-carbamic acid oxetan-3-yl ester (59)

The title compound was prepared analogously to example C58, but oxetane-3-ol was used instead of 1-fluoropropane-2-ol in step c. The title compound was purified by preparative HPLC-MS (23-24% MeCN in MQ with 0.01 M $NH_3$). LCMS-ES-478.36.

Example 60

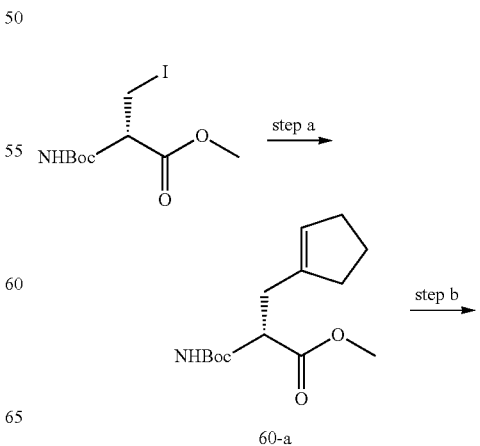

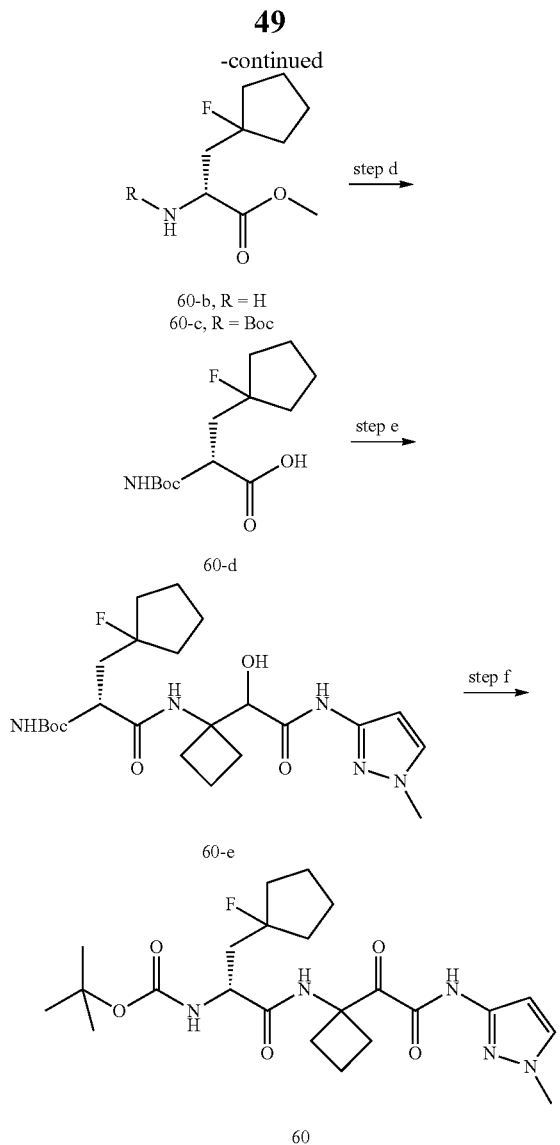

Step a) 2-tert-Butoxycarbonylamino-3-iodo-propionic acid methyl ester (60-a)

To a three necked flask charged with zinc dust (2.23 g, 34.1 mmol) under an $N_2$ atmosphere DMF (13 mL) was added. The suspension was efficiently stirred and $I_2$ (0.20 g, 0.80 mmol) was added. ((S)-2-[(tert-Butoxycarbonyl)amino]-3-iodopropionic acid methyl ester (4.50 g, 13.7 mmol) was added in one portion, and immediately after more $I_2$ (0.20 g, 0.80 mmol) and the stirring was continued for 2 h. Negishi coupling was then effected by addition in direct sequence of: $Pd_2\,dba_3$ (315 mg, 0.34 mmol), 2-dicyclohexylphosphino-2',6'-dimethoxybiphenyl (279 mg, 0.68 mmol), and 1-bromocyclopentene (2.32 g, 15.8 mmol) in DMF (4 mL). The reaction was stirred over night. DCM (25 mL) was added and the mixture was filtered, the solids were washed with further DCM, water (30 mL) was added and the phases were separated. The aqueous phase was extracted with DCM (2×20 mL) and the combined organic phases were washed with $H_2O$ (20 mL), dried $MgSO_4$, filtered and evaporated. The residue was purified by gradient silica gel chromatography (4-16% EtOAc in iso-hexane) which gave the title compound 1.24 g (30%). GC-MS EI m/z 213 (w), 196 (w), 152, 88, 57, 41.

Step b) 2-Amino-3-(1-fluoro-cyclopentyl)-propionic acid methyl ester (60-b)

The alkene product from the previous step (1.24 g, 4.62 mmol) was dissolved in toluene (10 mL) in a Teflon bottle which was cooled to 0° C. and the solution was stirred vigorously. HF-pyridine (70% HF, 8 mL) was added. The reaction was quenched when no further conversion could be detected by LC-MS ES+. The reaction mixture was carefully transferred to a flask containing a stirred $CaCO_3$ slurry (28 g) in $H_2O$ (100 mL) and DCM (50 mL) at 0° C. The pH was checked and adjusted to ~10 by addition of sat aq $Na_2CO_3$. The suspension was stirred briskly for 30 min Celite (16 g) was added to the quenched reaction mixture. The suspension was filtered and the filter cake was washed with DCM (100 mL in portions) and $H_2O$ (50 mL). The phases were separated and the aqueous layer was extracted with DCM (2×40 mL). The combined organic phases were washed with sat aq $NaHCO_3$ (40 mL) and evaporated. The crude product was used in the next step without further purification.

Step c) 2-tert-Butoxycarbonylamino-3-(1-fluoro-cyclopentyl)-propionic acid methyl ester (60-c)

The crude amino ester product from the previous step (0.94 g, approx 4.62 mmol) was dissolved in 1,4-dioxane (10 mL), aq sat $NaHCO_3$ (15 mL) was added and the mixture was stirred and cooled to 0° C. $Boc_2O$ (1.06 g, 4.85 mmol, in 10 mL 1,4-dioxane) was added. The reaction was allowed to reach rt and was stirred for 1 h. $Et_2O$ (30 mL) and $H_2O$ (20 mL) were added and the layers were separated. The aqueous phase was extracted with $Et_2O$ (2×25 mL). The combined organic phases were washed with $H_2O$ and brine (20 mL each), dried ($MgSO_4$), filtered and evaporated. The product was purified by gradient silica gel chromatography (2-17% EtOAc in iso-hexane). This gave the tert-butoxycarbonylamino ester product (391 mg, 29% in two steps). GC-MS m/z EI 230 (w), 196 (w), 174, 110, 59, 57, 41.

Step d) 2-tert-Butoxycarbonylamino-3-(1-fluoro-cyclopentyl)-propionic acid (60-d)

The methyl ester from the previous step (391 mg, 1.35 mmol) was dissolved in MeCN (6 mL) and THF (6 mL). The solution was stirred and an aqueous solution of LiOH (0.5 M, 2.7 mmol, 5.4 mL) was added. The mixture was stirred for 30 min then acidified with 1M HCl (6 mL) and immediately diluted with EtOAc (20 mL) and $H_2O$ (20 mL). The phases were separated and the organic layer was extracted with EtOAc (2×20 mL). The combined organic phases were washed a 1:1 mixture of 1M HCl and brine (20 mL), dried $Na_2SO_4$, filtered and evaporated. The product was purified by gradient silica gel chromatography (10-30% EtOAc in iso-hexane with 1% MeOH and 0.25% AcOH throughout), which gave the title compound (345 mg, 93%). αD20: +16.8 (c 1.0, MeOH). LC-MS m/z ES+ 200.1, ES− 274.1.

Step e) (2-(1-Fluoro-cyclopentyl)-1-{1-[(hydroxy-(1-methyl-1H-pyrazol-3-ylcarbamoyl)-methyl]-cyclobutylcarbamoyl}-ethyl)-carbamic acid tert-butyl ester (60-e)

Compound 9-a (185 mg, 0.57 mmol) was dissolved in 2 mL MeOH and treated with 4 M HCl in dioxane (4 mL). The reaction was stirred for 30 min whereafter the solution was degassed and freeze dried to yield the deprotected dihydrochloric acid salt in quantitative yield. This material was reacted with the acid C60-d (177 mg, 0.57 mmol) according to the procedure described for example C58, step a. The product was purified by gradient silica gel chromatography (0-6% MeOH in DCM) to yield 259 mg (94%). LCMS-ES+ 482.2.

Step f) {2-(1-Fluoro-cyclopentyl)-1-[1-(1-methyl-1H-pyrazol-3-ylaminooxalyl)-cyclobutylcarbamoyl]-ethyl}-carbamic acid tert-butyl ester (60)

The alcohol 60-e (40 mg, 0.083 mmol) was oxidised according to the procedure described in example C1, step d. The title compound (18 mg, 43%) was isolated by preparative HPLC-MS (30-35% MeCN in MQ with 0.01 M NH3 throughout). LCMS ES+ 480.5.

Example 61

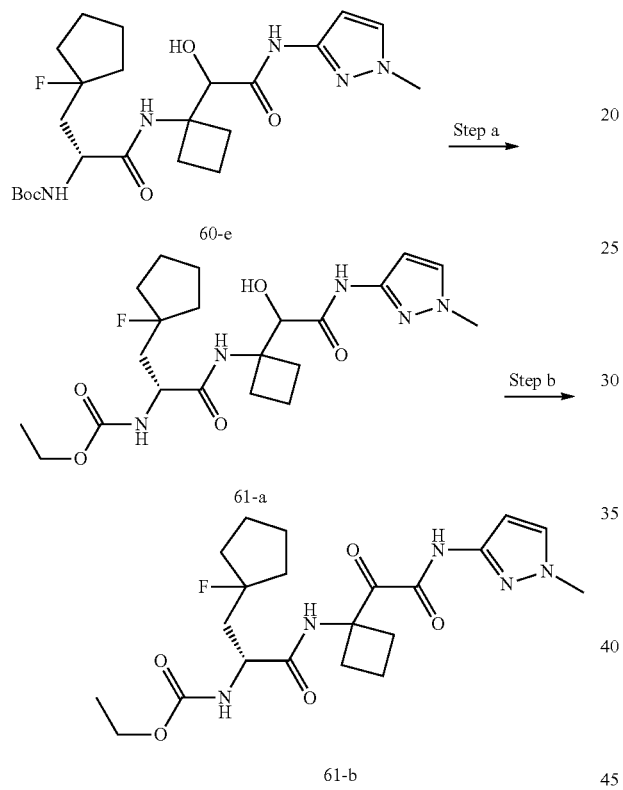

Step a) (2-(1-Fluorocyclopentyl)-1-{1-[(hydroxy-(1-methyl-1H-pyrazol-3-1carbamoyl)-methyl]-cyclobutylcarbamoyl}-ethyl)-carbamic acid ethyl ester (61-a)

Compound 60-e (212 mg, 0.44 mmol) was reacted with 4 M HCl in dioxane as described in Example 60 step e, which gave the deprotected dihydrochloride salt in quantitative yield. LCMS-ES+ 382.2. 50 mg (0.11 mmol) of this material was slurried in DCM (1 mL) and DIPEA (62 µL, 0.35 mmol) was added and the mixture was cooled to 0° C. and stirred until the solution was clear. Ethyl chloroformate (0.11 M in DCM, 0.9 mL) was added dropwise and the solution was stirred for 30 min Et₂O (10 mL) and sat aq NaHCO₃ (7 mL) was added and the phases were separated. The aqueous phase was extracted with EtOAc (2×5 mL) and the combined organic phases were washed with sat aq NaHCO₃ (7 mL) and evaporated which gave crude title compound which was used as such in the next step.

Step b) {2-(1-Fluoro-cyclopentyl)-1-[1-(1-methyl-1H-pyrazol-3-ylaminooxalyl)-cyclobutylcarbamoyl]-ethyl}-carbamic acid ethyl ester (61)

The crude alcohol 61-a was oxidised according to the procedure described in Example C1, step d. The title compound (18 mg, 32% over two steps) was isolated by preparative HPLC-MS (25-40% MeCN in MQ with 0.01 M NH₃). LCMS ES+ 452.5.

Example 62

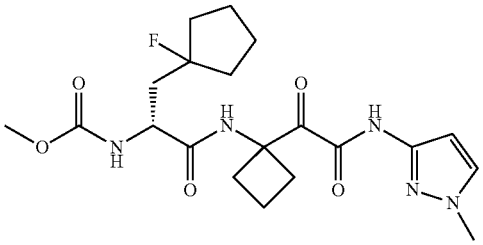

{2-(1-Fluoro-cyclopentyl)-1-[1-(1-methyl-1H-pyrazol-3-ylaminooxalyl)-cyclobutylcarbamoyl]-ethyl}-carbamic acid methyl ester (62)

The title compound was prepared according to a procedure analogous to the one described in Example 61 but in step a, methyl chloroformate was used instead of ethyl chloroformate. The title compound was purified by preparative HPLC-MS (25-30% MeCN in MQ with 0.01 M NH₃). LCMS-ES+ 438.5.

Examples 63-72

The compounds illustrated in the table below were prepared analogously to the procedure outlined in Example 1 using the appropriate $R^{1a}R^{1b}$ amines, P1/P2 building blocks and chloroformate, followed by Dess Martin oxidation to the end product α-keto amide.

TABLE 5

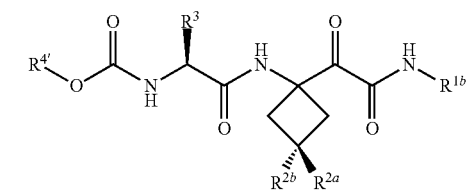

| Ex. | $R^{4'}$ | $R^3$ | $R^{2a}$ | $R^{2b}$ | $R^{1b}$ | [M + H]⁺ |
|---|---|---|---|---|---|---|
| 63 | ethyl | 1-fluorocyclopentylmethyl | H | H | 3-(4-methylpiperazin-1-yl)-propyl | 512.2 |

TABLE 5-continued

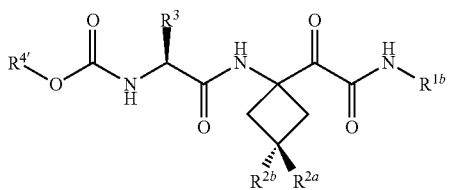

| Ex. | R⁴' | R³ | R²ᵃ | R²ᵇ | R¹ᵇ | [M + H]⁺ |
|---|---|---|---|---|---|---|
| 64 | ethyl | 1-fluorocyclopentylmethyl | H | H | 2-methoxyethyl | 430.2 |
| 65[1] | ethyl | 1-fluorocyclopentylmethyl | F | H | methyl | 402.4[3] |
| 66[1,2] | t-butyl | 3-(R/S)-difluorocyclopentylmethyl | H | H | 1-methylpyrazol-3-yl | 498.6 |
| 67[1] | ethyl | 3-(R/S)-difluorocyclopentylmethyl | H | H | 1-methylpyrazol-3-yl | 470.4 |
| 68 | ethyl | 1-fluorocyclopentylmethyl | OMe | H | 1-methylpyrazol-3-yl | 482.5 |
| 69 | isobutyl | 1-fluorocyclopentylmethyl | OMe | H | 1-methylpyrazol-3-yl | 510.3 |
| 70 | ethyl | 1-methyclopentylmethyl | OMe | H | 1-methylpyrazol-3-yl | 478.3 |
| 71[2] | ethyl | 1-fluorocyclopentylmethyl | H | OMe | 1-methylpyrazol-3-yl | 482.5 |
| 72 | t-butyl | 1-fluorocyclopentylmethyl | H | H | 3-(4-methyl-piperazin-1-yl)-propyl | 540.2 |

[1]Removal of the Boc group was performed using 4M HCl in dioxane.
[2]Step a was performed using the methyl ester of the P1-building block and an excess of 30% MeNH₂ in EtOH at 60° C. over three days. The reaction mixture was concentrated and the crude was used in the next step.
[3]MS was measured in negative mode, i.e. peak is [M − H]⁻.

Example 73

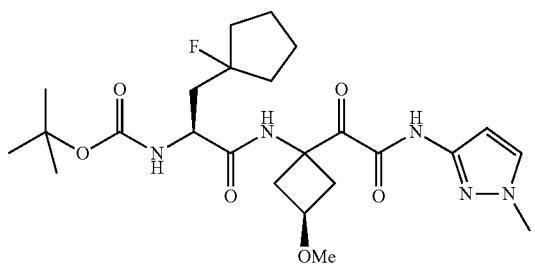

{2-(1-Fluoro-cyclopentyl)-1-[3-methoxy-1-(1-methyl-1H-pyrazol-3-ylaminooxalyl)-cyclobutylcarbamoyl]-ethyl}-carbamic acid tert-butyl ester (73)

The title compound was prepared according to the procedure outlined in Example 9, using the appropriate building blocks. The pure isomer of building BB8 was achieved by separation of the enantiomeric mixture obtained in the preparation of BB4-a. [M+H]⁺ 510.5.

Biological Examples

Determination of Cathepsin K Proteolytic Catalytic Activity

Convenient assays for cathepsin K are carried out using human recombinant enzyme, such as that described in PDB.
ID BC016058 standard; mRNA; HUM; 1699 BP.
DE *Homo sapiens* cathepsin K (pycnodysostosis), mRNA (cDNA clone MGC:23107
RX MEDLINE; RX PUBMED; 12477932.
DR RZPD; IRALp962G1234.
DR SWISS-PROT; P43235;
The recombinant cathepsin K can be expressed in a variety of commercially available expression systems including *E. coli*, *Pichia* and Baculovirus systems. The purified enzyme is activated by removal of the prosequence by conventional methods.

Standard assay conditions for the determination of kinetic constants used a fluorogenic peptide substrate, typically H-D-Ala-Leu-Lys-AMC, and were determined in either 100 mM Mes/Tris, pH 7.0 containing 1 mM EDTA and 10 mM 2-mercaptoethanol or 100 mM Na phosphate, 1mM EDTA, 0.1% PEG4000 pH 6.5 or 100 mM Na acetate, pH 5.5 containing 5 mM EDTA and 20 mM cysteine, in each case optionally with 1M DTT as stabiliser. The enzyme concentration used was 5 nM. The stock substrate solution was prepared at 10 mM in DMSO. Screens were carried out at a fixed substrate concentration of 60 µM and detailed kinetic studies with doubling dilutions of substrate from 250 µM. The total DMSO concentration in the assay was kept below 3%. All assays were conducted at ambient temperature. Product fluorescence (excitation at 390 nm, emission at 460 nm) was monitored with a Labsystems Fluoroskan Ascent fluorescent plate reader. Product progress curves were generated over 15 minutes following generation of AMC product.

Cathepsin S Ki Determination

The assay uses baculovirus-expressed human cathepsin S and the boc-Val-Leu-Lys-AMC fluorescent substrate available from Bachem in a 384 well plate format, in which 7 test compounds can be tested in parallel with a positive control comprising a known cathepsin S inhibitor comparator.

Substrate Dilutions

280 µL/well of 12.5% DMSO are added to rows B-H of two columns of a 96 deep well polypropylene plate. 70 µL/well of substrate is added to row A. 2×250 µL/well of assay buffer (100 mM Na phosphate, 100 mM NaCl, pH 6.5) is added to row A, mixed, and double diluted down the plate to row H.

Inhibitor Dilutions

100 µL/well of assay buffer is added to columns 2-5 and 7-12 of 4 rows of a 96 well V bottom polypropylene plate. 200 µL/well of assay buffer is added to columns 1 and 6.

The first test compound prepared in DMSO is added to column 1 of the top row, typically at a volume to provide between 10 and 30 times the initially determined rough $K_i$. The rough $K_i$ is calculated from a preliminary run in which 10

μL/well of 1 mM boc-VLK-AMC (1/10 dilution of 10 mM stock in DMSO diluted into assay buffer) is dispensed to rows B to H and 20 μl/well to row A of a 96 well Microfluor™ plate. 2 μl of each 10 mM test compound is added to a separate well on row A, columns 1-10. Add 90 μl assay buffer containing 1 mM DTT and 2 nM cathepsin S to each well of rows B-H and 180 μl to row A. Mix row A using a multichannel pipette and double dilute to row G. Mix row H and read in the fluorescent spectrophotometer. The readings are Prism data fitted to the competitive inhibition equation, setting S=100 μM and $K_M$=100 μM to obtain an estimate of the $K_i$, up to a maximum of 100 μM.

The second test compound is added to column 6 of the top row, the third to column 1 of the second row etc. Add 1 μL of comparator to column 6 of the bottom row. Mix column 1 and double dilute to column 5. Mix column 6 and double dilute to column 10.

Using an 8-channel multistepping pipette set to 5×10 μL, distribute 10 μL/well of substrate to the 384 well assay plate. Distribute the first column of the substrate dilution plate to all columns of the assay plate starting at row A. The tip spacing of the multichannel pipette will correctly skip alternate rows. Distribute the second column to all columns starting at row B.

Using a 12-channel multistepping pipette set to 4×10 μL, distribute 10 μL/well of inhibitor to the 384 well assay plate. Distribute the first row of the inhibitor dilution plate to alternate rows of the assay plate starting at A1. The tip spacing of the multichannel pipette will correctly skip alternate columns. Similarly, distribute the second, third and fourth rows to alternate rows and columns starting at A2, B1 and B2 respectively.

Mix 20 mL assay buffer and 20 μL 1M DTT. Add sufficient cathepsin S to give 2 nM final concentration.

Using the a distributor such as a Multidrop 384, add 30 μL/well to all wells of the assay plate and read in fluorescent spectrophotometer such as an Ascent.

Fluorescent readings, (excitation and emission wavelengths 390 nm and 460 nm respectively, set using bandpass filters) reflecting the extent of enzyme cleavage of the fluorescent substrate, notwithstanding the inhibitor, are linear rate fitted for each well.

Fitted rates for all wells for each inhibitor are fitted to the competitive inhibition equation using SigmaPlot 2000 to determine V, Km and Ki values.

Cathepsin L Ki

The procedure above with the following amendments is used for the determination of Ki for cathepsin L.

The enzyme is commercially available human cathepsin L (for example Calbiochem). The substrate is H-D-Val-Leu-Lys-AMC available from Bahcem. The assay buffer is 100 mM sodium acetate 1 mM EDTA, pH5.5) The DMSO stock (10 mM in 100% DMSO) is diluted to 10% in assay buffer. Enzyme is prepared at 5 nM concentration in assay buffer plus 1 mM dithiothreitol just before use. 2 μL of 10 mM inhibitor made up in 100% DMSO is dispensed into row A. 10 μL of 50 μM substrate (=1/200 dilution of 10 mM stock in DMSO, diluted in assay buffer).

Inhibition Studies

Potential inhibitors are screened using the above assay with variable concentrations of test compound. Reactions were initiated by addition of enzyme to buffered solutions of substrate and inhibitor. $K_i$ values were calculated according to equation 1.

$$v_0 = \frac{VS}{K_M\left(1 + \frac{I}{K_i}\right) + S} \quad (1)$$

where $v_0$ is the velocity of the reaction, V is the maximal velocity, S is the concentration of substrate with Michaelis constant of $K_M$, and I is the concentration of inhibitor. The inhibition of cathepsin S, cathepsin K and cathepsin L exhibited by a selection of the compounds of the invention represented as Ki values in nM is presented in Table 1.

TABLE 1

| Example | Ki Cat. S | Ki Cat. K | Ki Cat. L |
|---------|-----------|-----------|-----------|
| 1 | 3.6 | 1100 | 4800 |
| 4 | 11 | 430 | 3300 |
| 8 | 1.0 | 1200 | 3300 |
| 10 | 0.55 | 170 | 360 |
| 11 | 1.0 | 610 | 1100 |
| 19 | 4.7 | 150 | 330 |
| 20 | 30 | 95000 | >200000 |
| 22 | 14 | 3800 | 25000 |
| 24 | 7.8 | 4400 | 10000 |
| 31 | 1.8 | 410 | 1200 |
| 37 | 2.6 | 280 | 2000 |
| 41 | 0.8 | 190 | 940 |
| 45 | 6 | 1100 | 850 |
| 49 | 0.65 | 240 | 660 |
| 50 | 0.65 | 100 | 560 |
| 52 | 0.4 | 98 | 270 |
| 56 | 1.8 | 440 | 990 |
| 57 | 0.79 | 290 | 720 |
| 59 | 2.2 | 340 | 2100 |
| 63 | 22 | 1400 | 4900 |
| 68 | 1.1 | 640 | 2400 |
| 70 | 0.7 | 1400 | 2100 |
| 73 | 0.8 | 250 | 1100 |

The compounds of Formula II are thus potent inhibitors of cathepsin S and yet selective over the closely related cathepsin K and L.

Permeability

This experiment measures transport of inhibitors through the cells of the human gastroenteric canal. The assay uses the well known Caco-2 cells with a passage number between 40 and 60.

Apical to Basolateral Transport

Generally every compound will be tested in 2-4 wells. The basolateral and the apical wells will contain 1.5 mL and 0.4 mL transport buffer (TB), respectively, and the standard concentration of the tested substances is 10 μM. Furthermore all test solutions and buffers will contain 1% DMSO. Prior to the experiment the transport plates are pre-coated with culture medium containing 10% serum for 30 minutes to avoid non-specific binding to plastic material. After 21 to 28 days in culture on filter supports, the cells are ready for permeability experiments.

Transport plate no 1 comprises 3 rows of 4 wells each. Row 1 is denoted Wash, row 2 "30 minutes" and row 3 "60 minutes". Transport plate no 2 comprises 3 rows of 4 wells, one denoted row 4 "90 minutes", row 5 "120 minutes and the remaining row unassigned.

The culture medium from the apical wells is removed and the inserts are transferred to a wash row (No. 1) in a transport plate (plate no.1) out of 2 plates without inserts, which have already been prepared with 1.5 mL transport buffer (HBSS, 25 mM HEPES, pH 7.4) in rows 1 to 5. In A→B screening the TB in basolateral well also contains 1% Bovine Serum Albumin 0.5 mL transport buffer (HBSS, 25 mM MES, pH 6.5) is added to the inserts and the cell monolayers equilibrated in the transport buffer system for 30 minutes at 37° C. in a polymix shaker. After being equilibrated to the buffer system the Transepithelial electrical resistance value (TEER) is measured in each well by an EVOM chop stick instrument. The TEER values are usually between 400 to 1000Ω per well (depends on passage number used).

The transport buffer (TB, pH 6.5) is removed from the apical side and the insert is transferred to the 30 minutes row (No. 2) and fresh 425 μL TB (pH 6.5), including the test substance is added to the apical (donor) well. The plates are incubated in a polymix shaker at 37° C. with a low shaking velocity of approximately 150 to 300 rpm.

After 30 minutes incubation in row 2, the inserts are moved to new pre-warmed basolateral (receiver) wells every 30 minutes; row 3 (60 minutes), 4 (90 minutes) and 5 (120 minutes).

25 μL samples are taken from the apical solution after ~2 minutes and at the end of the experiment. These samples represent donor samples from the start and the end of the experiment.

300 μL will be taken from the basolateral (receiver) wells at each scheduled time point and the post value of TEER is measured at the end the experiment. To all collected samples acetonitrile will be added to a final concentration of 50% in the samples. The collected samples will be stored at −20° C. until analysis by HPLC or LC-MS.

Basolateral to Apical Transport

Generally every compound will be tested in 2-4 wells. The basolateral and the apical wells will contain 1.55 mL and 0.4 mL TB, respectively, and the standard concentration of the tested substances is 10 μM. Furthermore all test solutions and buffers will contain 1% DMSO. Prior to the experiment the transport plates are precoated with culture medium containing 10% serum for 30 minutes to avoid nonspecific binding to plastic material.

After 21 to 28 days in culture on filter supports the cells are ready for permeability experiments. The culture medium from the apical wells are removed and the inserts are transferred to a wash row (No. 1) in a new plate without inserts (Transport plate).

The transport plate comprises 3 rows of 4 wells. Row 1 is denoted "wash" and row 3 is the "experimental row". The transport plate has previously been prepared with 1.5 mL TB (pH 7.4) in wash row No. 1 and with 1.55 mL TB (pH 7.4), including the test substance, in experimental row No. 3 (donor side).

0.5 mL transport buffer (HBSS, 25 mM MES, pH 6.5) is added to the inserts in row No. 1 and the cell monolayers are equilibrated in the transport buffer system for 30 minutes, 37° C. in a polymix shaker. After being equilibrated to the buffer system the TEER value is measured in each well by an EVOM chop stick instrument.

The transport buffer (TB, pH 6.5) is removed from the apical side and the insert is transferred to row 3 and 400 μL fresh TB, pH 6.5 is added to the inserts. After 30 minutes 250 μL is withdrawn from the apical (receiver) well and replaced by fresh transport buffer. Thereafter 250 μL samples will be withdrawn and replaced by fresh transport buffer every 30 minutes until the end of the experiment at 120 minutes, and finally a post value of TEER is measured at the end of the experiment. A 25 μL samples will be taken from the basolateral (donor) compartment after ~2 minutes and at the end of the experiment. These samples represent donor samples from the start and the end of the experiment.

To all collected samples acetonitrile will be added to a final concentration of 50% in the samples. The collected samples will be stored at −20° C. until analysis by HPLC or LC-MS.

Calculation

Determination of the cumulative fraction absorbed, $FA_{cum}$, versus time. $FA_{cum}$ is calculated from:

$$FA_{cum} = \sum \frac{C_{Ri}}{C_{Di}}$$

Where $C_{Ri}$ is the receiver concentration at the end of the interval i and $C_{Di}$ is the donor concentration at the beginning of interval i. A linear relationship should be obtained.

The determination of permeability coefficients ($P_{app}$, cm/s) are calculated from:

$$P_{app} = \frac{(k \cdot V_R)}{(A \cdot 60)}$$

where k is the transport rate (min$^{-1}$) defined as the slope obtained by linear regression of cumulative fraction absorbed ($FA_{cum}$) as a function of time (min), $V_R$ is the volume in the receiver chamber (mL), and A is the area of the filter (cm$^2$).

| Reference compounds | | |
|---|---|---|
| Category of absorption in man | Markers | absorption in man (%) |
| PASSIVE TRANSPORT | | |
| Low (0-20%) | Mannitol | 16 |
| | Methotrexate | 20 |
| Moderate (21-75%) | Acyclovir | 30 |
| High (76-100%) | Propranolol | 90 |
| | Caffeine | 100 |
| ACTIVE TRANSPORT | | |
| Amino acid transporter | L-Phenylalanine | 100 |
| ACTIVE EFFLUX | | |
| PGP-MDR1 | Digoxin | 30 |

Greater permeability through the gastrointestinal tissue is advantageous in that it allows for the use of a smaller dose to achieve similar levels of exposure to a less permeable compound administered in a higher dose. A low dose is advantageous in that it minimizes the cost of goods for a daily dose, which is a crucial parameter in a drug which is taken for protracted time periods.

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:
1. A compound of Formula II:

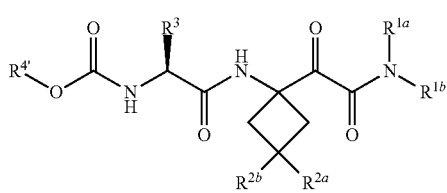

(II)

wherein
$R^{1a}$ is H; and
$R^{1b}$ is $C_1$-$C_6$alkyl, optionally substituted with 1-3 substituents independently selected from: halo, hydroxy, cyano, azido, $C_1$-$C_4$haloalkyl, $C_1$-$C_4$alkoxy, $C_1$-$C_4$haloalkoxy, $C_1$-$C_4$alkoxycarbonyl, $C_1$-$C_4$alkylcarbonyl, amine, $C_1$-$C_4$alkylamine, $C_1$-$C_4$dialkylamine, $C_1$-$C_4$alkylsulfonyl, $C_1$-$C_4$alkylsulfonylamino, aminocarbonyl, aminosulphonyl, Carbocyclyl and Het; or
$R^{1b}$ is Carbocyclyl or Het; or
$R^{1a}$ and $R^{1b}$ together with the N atom to which they are attached define a saturated cyclic amine with 3-6 ring atoms;
wherein the Carbocyclyl, Het or cyclic amine is optionally substituted with 1-3 substituents independently selected from halo, hydroxy, cyano, azido, $C_1$-$C_4$alkyl, $C_1$-$C_4$haloalkyl, $C_1$-$C_4$alkoxy, $C_1$-$C_4$haloalkoxy, $C_1$-$C_4$alkoxycarbonyl, $C_1$-$C_4$alkylcarbonyl, amine, $C_1$-$C_4$alkylamine, $C_1$-$C_4$dialkylamine, $C_1$-$C_4$alkylsulfonyl, $C_1$-$C_4$alkylsulfonylamino, aminocarbonyl, aminosulphonyl, RxOOC—$C_0$-$C_2$alkylene (where Rx is H, $C_1$-$C_4$alkyl or $C_1$-$C_4$haloalkyl), phenyl, benzyl or $C_3$-$C_6$cycloalkyl$C_0$-$C_2$alkylene;
wherein the phenyl, benzyl or cycloalkyl moiety is optionally substituted with 1-3 substituents independently selected from halo, $C_1$-$C_4$alkyl, $C_1$-$C_4$haloalkyl or $C_1$-$C_4$alkoxy);
$R^{2a}$ and $R^{2b}$ are independently selected from H, halo, $C_1$-$C_4$alkyl, $C_1$-$C_4$haloalkyl, $C_1$-$C_4$alkoxy, or $R^{2a}$ and $R^{2b}$ together with the carbon atom to which they are attached form a $C_3$-$C_6$cycloalkyl;
$R^3$ is a $C_5$-$C_{10}$ alkyl, optionally substituted with 1-3 substituents independently selected from halo, $C_1$-$C_4$haloalkyl, $C_1$-$C_4$alkoxy, $C_1$-$C_4$haloalkoxy; or
$R^3$ is a $C_2$-$C_4$alkyl chain with at least 2 chloro or 3 fluoro substituents; or
$R^3$ is $C_3$-$C_7$cycloalkylmethyl, optionally substituted with 1-3 substituents independently selected from $C_1$-$C_4$alkyl, halo, $C_1$-$C_4$haloalkyl, $C_1$-$C_4$alkoxy, $C_1$-$C_4$haloalkoxy;
$R^{4'}$ is $C_1$-$C_6$alkyl, $C_1$-$C_6$haloalkyl or oxetan-3-yl;
Het is a stable, monocyclic or bicyclic, saturated, partially saturated or aromatic ring system containing 1-4 heteroatoms independently selected from O, S and N, each ring having 5 or 6 ring atoms;
Carbocyclyl is $C_3$-$C_6$cycloalkyl, $C_5$-$C_6$cycloalkenyl or phenyl;
or a pharmaceutically acceptable salt, hydrate or N-oxide thereof.
2. A compound according to claim 1, wherein $R^{1b}$ is methyl, cyclopropyl, 1-phenylethyl, or a 5 or 6 membered heterocyclic ring containing 1-3 nitrogen atoms and 0 or 1 sulphur atoms, the cyclopropyl, phenyl or heterocyclic ring being optionally substituted with up to three substituents independently selected from $C_1$-$C_4$alkyl, halo, $C_1$-$C_4$haloalkyl, $C_1$-$C_4$alkoxy, $C_1$-$C_4$haloalkoxy, $C_1$-$C_4$alkoxycarbonyl, $C_1$-$C_4$alkylcarbonyl, amine, $C_1$-$C_4$alkylamine, $C_1$-$C_4$-dialkylamine, $C_1$-$C_4$alkylsulfonyl, $C_1$-$C_4$alkylsulfonylamino, aminocarbonyl, aminosulphonyl, RxOOC—$C_0$-$C_2$alkylene (where Rx is H or $C_1$-$C_4$alkyl) or $C_3$-$C_6$cycloalkyl$C_0$-$C_2$alkylene or benzyl (the cycloalkyl, or the phenyl ring of the benzyl being optionally substituted with 1-3 substituents selected from $C_1$-$C_4$alkyl, halo, $C_1$-$C_4$haloalkyl, $C_1$-$C_4$alkoxy, $C_1$-$C_4$haloalkoxy).
3. A compound according to claim 2, wherein the heterocyclic ring is pyrrolyl, pyrazolyl, imidazolyl, triazolyl, thiazolyl, or thiadiazolyl, any of which is optionally substituted with $C_1$-$C_4$alkyl, halo, $C_1$-$C_4$haloalkyl, $C_1$-$C_4$alkoxy, $C_3$-$C_6$cycloalkyl or $C_3$-$C_6$cycloalkylmethyl.
4. A compound according to claim 3, wherein the heterocyclic ring is pyrazol-1-yl, optionally substituted with $C_1$-$C_4$alkyl, halo, $C_1$-$C_4$haloalkyl, $C_1$-$C_4$alkoxy or cyclopropyl.
5. A compound according to claim 4, wherein the pyrazolyl is N-substituted with $C_1$-$C_4$alkyl, such as ethyl or methyl.
6. A compound according to claim 1, wherein $R^{2a}$ and $R^{2b}$ are both F.
7. A compound according to claim 1, wherein one of $R^{2a}$ and $R^{2b}$ is H, and the other is Cl, F, $F_3C$ or MeO.
8. A compound according to claim 1, wherein $R^{2a}$ and $R^{2b}$ are both H.
9. A compound according to claim 1, wherein $R^3$ is t-butylmethyl, cyclobutylmethyl, 1-methylcyclobutylmethyl or 1-methylcyclopentylmethyl, any of which is optionally substituted with one or two F or MeO.
10. A compound according to claim 1, wherein $R^3$ is 1-methylcyclopentylmethyl or 1-fluorocyclopentylmethyl.
11. A compound according to claim 1, wherein $R^{4'}$ is $C_1$-$C_4$alkyl.
12. A compound according to claim 11, wherein $R^{4'}$ is methyl or ethyl.
13. A pharmaceutical composition comprising a compound according to claim 1 and a pharmaceutically acceptable vehicle.
14. A method for the treatment of a disorder selected from the group consisting of:
psoriasis, idiopathic thrombocytopenic purpura (ITP), rheumatoid arthritis (RA), multiple sclerosis (MS), myasthenia gravis (MG), Sjögrens syndrome, Grave's disease, systemic lupus erythematosis (SLE), allergic rhinitis, asthma, atherosclerosis, chronic obstructive pulmonary disease (COPD), and neuropathic pain;
said method comprising the administration of an effective amount of a compound as defined in claim 1 to a human or animal afflicted with the disorder.
15. The compound according to claim 1, wherein
$R^{1b}$ is methylpyrazolyl;
$R^{2a}$ and $R^{2b}$ are each H;
$R^3$ is 1-fluorocyclopentylmethyl; and
$R^{4'}$ is ethyl.
16. A pharmaceutical composition comprising a compound according to claim 15 and a pharmaceutically acceptable vehicle therefor.
17. A method for the treatment of neuropathic pain, the method comprising the administration of an effective amount of a compound as defined in claim 15 to a human or animal afflicted with the disorder.

* * * * *